(12) United States Patent
Ramanand et al.

(10) Patent No.: US 11,955,303 B2
(45) Date of Patent: Apr. 9, 2024

(54) PERFORMANCE IMPROVEMENT UNIT FOR PULSED-ULTRAVIOLET DEVICES

(71) Applicant: Anram Holdings, Mississauga (CA)

(72) Inventors: Prakash Valentino Ramanand, Burlington (CA); Manjinder Singh Dhillon, Milton (CA)

(73) Assignee: Anram Holdings, Oakville (CA)

( * ) Notice: Subject to any disclaimer, the term of this patent is extended or adjusted under 35 U.S.C. 154(b) by 0 days.

(21) Appl. No.: 18/156,540

(22) Filed: Jan. 19, 2023

(65) Prior Publication Data

US 2023/0298842 A1 Sep. 21, 2023

Related U.S. Application Data

(63) Continuation of application No. 17/018,443, filed on Sep. 11, 2020, now Pat. No. 11,587,753, which is a continuation of application No. 16/689,629, filed on Nov. 20, 2019, now Pat. No. 10,811,208.

(60) Provisional application No. 62/769,779, filed on Nov. 20, 2018.

(51) Int. Cl.
| | |
|---|---|
| *H01H 71/04* | (2006.01) |
| *A61L 2/10* | (2006.01) |
| *H01H 83/20* | (2006.01) |
| *H05B 47/16* | (2020.01) |

(52) U.S. Cl.
CPC .......... *H01H 71/04* (2013.01); *H01H 83/20* (2013.01); *H05B 47/16* (2020.01); *A61L 2/10* (2013.01); *H01H 2219/036* (2013.01)

(58) Field of Classification Search
None
See application file for complete search history.

(56) References Cited

U.S. PATENT DOCUMENTS

| | | | |
|---|---|---|---|
| 6,388,849 B1 | 5/2002 | Rae | |
| 9,924,569 B2 * | 3/2018 | Wang | .................... H05B 45/46 |
| 2010/0259956 A1 | 10/2010 | Sadwick et al. | |
| 2013/0048569 A1 | 2/2013 | Ogut et al. | |

(Continued)

OTHER PUBLICATIONS

Intellectual Property India: Indian Examination Report relating to Indian application No. 202147026140, dated Dec. 30, 2022.

(Continued)

*Primary Examiner* — Jany Richardson
(74) *Attorney, Agent, or Firm* — Rowand LLP

(57) ABSTRACT

Embodiments of the present disclosure disclose a method for improving a performance of a pulsed-ultraviolet (PUV) device. The method includes monitoring an input current across a circuit breaker in communication with a UV lamp, where the input current is delivered by a power signal and is interrupted by the circuit breaker upon exceeding a predefined cut-off current; generating a pulse signal having a set of frequencies based on the power signal for driving the UV lamp, where the pulse signal is associated with a predetermined cut-off frequency that increases the input current beyond the cut-off current; determining a predefined threshold current less than the cut-off current; and configuring the pulse signal with multiple distinct pulse frequencies per second for a predefined configuration period based on the input current exceeding the threshold current. The distinct pulse frequencies per second include at least one pulse frequency greater than the cut-off frequency.

20 Claims, 13 Drawing Sheets

(56) References Cited

U.S. PATENT DOCUMENTS

2014/0063857 A1* 3/2014 Peng ................... H05B 45/382
                                                    363/16
2014/0354111 A1  12/2014 Jo et al.

OTHER PUBLICATIONS

International Search Report and Written Opinion relating to PCT/CA2019/051656, dated Feb. 20, 2020.
USPTO, Office Action relating to U.S. Appl. No. 17/018,443 dated Nov. 15, 2021.
USPTO, Notice of Allowance relating to U.S. Appl. No. 17/018,443 dated Oct. 19, 2022.
USPTO, Notice of Allowance relating to U.S. Appl. No. 16/689,629 dated Jun. 26, 2020.

* cited by examiner

Fixed, Single Frequency 29 Hz @5mins

Fixed, Single Frequency 29 Hz @10mins

Fixed, Single Frequency 30 Hz @3mins

Fixed, Single Frequency 30 Hz @5mins

Fixed, Single Frequency 30 Hz @10mins

Fixed, Single Frequency 33 Hz @3mins

Fixed, Single Frequency 33 Hz @5mins

Fixed, Single Frequency 33 Hz @10mins

Fixed, Single Frequency 28 Hz @5mins

Fixed, Single Frequency 28 Hz @10mins

Compound Frequencies (28 Hz, 29 Hz) @3mins

Compound Frequencies (28 Hz, 29 Hz) @5mins

Compound Frequencies (28 Hz, 29 Hz) @10mins

Compound Frequencies (28 Hz, 30 Hz) @3mins

Compound Frequencies (28 Hz, 30 Hz) @5mins

Compound Frequencies (28 Hz, 30 Hz) @10mins

PERFORMANCE IMPROVEMENT UNIT FOR PULSED-ULTRAVIOLET DEVICES

TECHNICAL FIELD

The present disclosure generally relates to pulsed-ultraviolet (PUV) devices and particularly relates to a performance improvement unit for PUV devices.

BACKGROUND

PUV devices are well-known in the modern cleaning industry and are steadily being adopted as an everyday tool for surface disinfection. Among other applications, a PUV device is employed to disinfect large areas such as rooms, halls, and corridors, and typically includes a circuit breaker for electrical safety and a UV lamp that emits PUV light for a predefined disinfection cycle or period. The circuit breaker interrupts an input current to the PUV device and shuts down the UV lamp if any electrical changes during operation increase the input current beyond a safe limit. Although such interruption safeguards against any potential electrical hazard, the PUV device is forced to be run for multiple disinfection cycles or longer durations to achieve an intended disinfection, thereby yielding a substandard operational performance.

SUMMARY

Traditionally, various parameters of a PUV disinfection device (or "PUV device") are adjusted to improve its operational performance, which is used in the present disclosure within the context of its broadest definition. One common approach to boost the operational performance includes increasing an applied voltage to a UV lamp of the PUV device for amplifying its UV output, e.g., intensity of UV light emitted therefrom. Since the UV output is limited by a voltage rating of the lamp, such increase in the applied voltage requires an existing UV lamp to be replaced with a new UV lamp having a relatively higher voltage rating. The new UV lamp with the higher voltage rating is generally expensive, adds to a replacement cost, and increases the manufacturing and/or operational costs of the PUV device.

Another typical approach includes a pulse frequency of the UV output being increased to raise the UV intensity. Any increase in the pulse frequency increases an applied power to the UV lamp per unit time, which then ramps up an input current to the PUV device often beyond a safe limit and trips an on-device circuit breaker for a given operating voltage of the UV lamp. As a result, the PUV device, or the UV lamp, is shutdown that disrupts a disinfection cycle, thereby leading to an ineffective disinfection of a target area. The on-device circuit breaker has to be reset to restart the disinfection cycle. Such unintended toggling of the PUV device, or the UV lamp, between the on and off states extends a total time required to disinfect the target area, thereby magnifying operational costs and user inconvenience. One traditional remedy to such tripping is deploying, additionally or alternatively, a new on-device circuit breaker that has a higher current rating, which often moots the purpose of a mains circuit breaker. Moreover, the new circuit breaker having the higher current rating is expensive and increases a manufacturing cost of the PUV device.

Yet another traditional approach includes an applied current to the UV lamp being variably increased over a disinfection period to increase the UV output. However, any variation in the applied current requires the applied voltage to the UV lamp being regulated to operate within safe limits of the input power thereto. Such need for simultaneous regulation of the applied voltage increases the operational complexity and signal delay, thereby limiting any rise in the UV output by voltage and current ratings of the UV lamp. Other existing approaches include running the PUV device, or a disinfection cycle thereof, for longer periods to increase an amount of UV light radiated on to the target area. However, such long-period operation of the PUV device increases the input current to the PUV device and repeatedly trips the on-device circuit breaker to disrupt the disinfection cycle, thereby resulting in an ineffective disinfection of the target area.

It may therefore be beneficial to provide systems and methods that improve the operational performance of PUV devices without disrupting a predefined disinfection cycle for given voltage and current ratings of the UV lamp.

One exemplary embodiment of the present disclosure includes a method for improving a performance of a pulsed-ultraviolet (PUV) device. The method may include monitoring, using a pulse generator coupled to a processor and a memory, an input current across a circuit breaker in electrical communication with a UV lamp. The input current may be delivered by a power signal and interrupted by the circuit breaker upon exceeding a predefined cut-off current. The method may also include generating, using the pulse generator, a pulse signal having a set of one or more pulse frequencies based on the power signal for driving the UV lamp, where the pulse signal may be associated with a predetermined cut-off frequency capable of increasing the input current beyond the predefined cut-off current; determining, using the pulse generator, a predefined threshold current for the circuit breaker, where the predefined threshold current may be less than the cut-off current; and configuring, using the pulse generator, the generated pulse signal with multiple distinct pulse frequencies per second for a predefined configuration period based on the input current exceeding the predefined threshold current. The multiple distinct pulse frequencies per second may include at least one pulse frequency being greater than the predetermined cut-off frequency.

One aspect of the present disclosure includes the distinct pulse frequencies per second further including at least one pulse frequency being less than the predetermined cut-off frequency.

Another aspect of the present disclosure includes the predefined cut-off current being relative to a preset current rating of the circuit breaker.

Yet another aspect of the present disclosure includes receiving a first control signal from a performance controller, where the first control signal may be configured to modulate one or more characteristics of a pulse frequency in the set to create a buffer period per second within the predefined configuration period, provided the set includes a single pulse frequency per second.

Still another aspect of the present disclosure includes the buffer period has zero pulse frequency.

A further aspect of the present disclosure includes receiving a second control signal from the performance controller, the second control signal being configured to drive the buffer period with a lowest frequency in a predefined group of upper frequencies if the single pulse frequency may be less than the predetermined cut-off frequency, where the predefined group of upper frequencies are greater than the predetermined cut-off frequency.

Another aspect of the present disclosure includes receiving a first control signal from a performance controller based on a number of distinct pulse frequencies per second in the set being greater than one, where the first control signal may be configured to select a highest frequency in the set, where the highest frequency may be greater than the predetermined cut-off frequency; and adjust the selected highest frequency by a predefined factor to a safe upper frequency belonging to a predefined group of upper frequencies greater than the predetermined cut-off frequency.

Still another aspect of the present disclosure includes receiving a second control signal from the performance controller based on each of the distinct pulse frequencies per second in the set being less than the predetermined cut-off frequency, where the second control signal may be configured to—select a lowest frequency in the set, where the lowest frequency may be less than the predetermined cut-off frequency; and adjust the selected lowest frequency to a highest frequency in a predefined group of lower frequencies less than the predetermined cut-off frequency.

Yet another aspect of the present disclosure includes multiple distinct pulse frequencies per second ranging from 2 Hz to 50 Hz.

A further aspect of the present disclosure includes multiple distinct pulse frequencies per second including non-consecutive pulse frequencies.

Another exemplary embodiment of the present disclosure includes a system for improving a performance of a pulsed-ultraviolet (PUV) device. The system includes a UV lamp for generating PUV light, a power supply providing a power signal carrying an input current, a circuit breaker, and a pulse generator. The circuit breaker may be in electrical communication with the power supply. The circuit breaker may be configured to interrupt the input current applied thereto upon exceeding a predefined cut-off current. The pulse generator may be in electrical communication with the circuit breaker and the UV lamp, where the pulse generator may be configured to: monitor the input current across the circuit breaker; generate a pulse signal having a set of one or more pulse frequencies based on the power signal for driving the UV lamp, where the pulse signal may be associated with a predetermined cut-off frequency capable of increasing the input current beyond the predefined cut-off current; determine a predefined threshold current for the circuit breaker, where the predefined threshold current may be less than the cut-off current; and configure the generated pulse signal with multiple distinct pulse frequencies per second for a predefined configuration period based on the input current exceeding the predefined threshold current, where the plurality of distinct pulse frequencies per second includes at least one pulse frequency being greater than the predetermined cut-off frequency.

One aspect of the present disclosure includes improving an electrical performance of the PUV device.

Another aspect of the present disclosure includes improving a disinfection performance of the PUV device.

Yet another exemplary embodiment may include a non-transitory computer-readable medium including computer-executable instructions for improving a performance of a pulsed-ultraviolet (PUV) device. The non-transitory computer readable medium may include instructions for monitoring an input current across a circuit breaker in electrical communication with a UV lamp. The input current may be delivered by a power signal and interrupted by the circuit breaker upon exceeding a predefined cut-off current. The non-transitory computer readable medium may also include instructions for generating a pulse signal having a set of one or more pulse frequencies based on the power signal for driving the UV lamp, where the pulse signal may be associated with a predetermined cut-off frequency capable of increasing the input current beyond the predefined cut-off current; determining a predefined threshold current for the circuit breaker, where the predefined threshold current may be less than the cut-off current; and configuring the generated pulse signal with multiple distinct pulse frequencies per second for a predefined configuration period based on the input current exceeding the predefined threshold current. The multiple distinct pulse frequencies per second may include at least one pulse frequency being greater than the predetermined cut-off frequency.

The above summary of exemplary embodiments is not intended to describe each disclosed embodiment or every implementation of the present disclosure. Other and further aspects and features of the disclosure will be evident from reading the following detailed description of the embodiments, which are intended to illustrate, not limit, the present disclosure.

BRIEF DESCRIPTION OF THE DRAWINGS

The illustrated embodiments of the subject matter will be best understood by reference to the drawings, wherein like parts are designated by like numerals throughout. The following description is intended only by way of example, and simply illustrates certain selected embodiments of devices, systems, and processes that are consistent with the subject matter as claimed herein.

DETAILED DESCRIPTION

Figure 1:
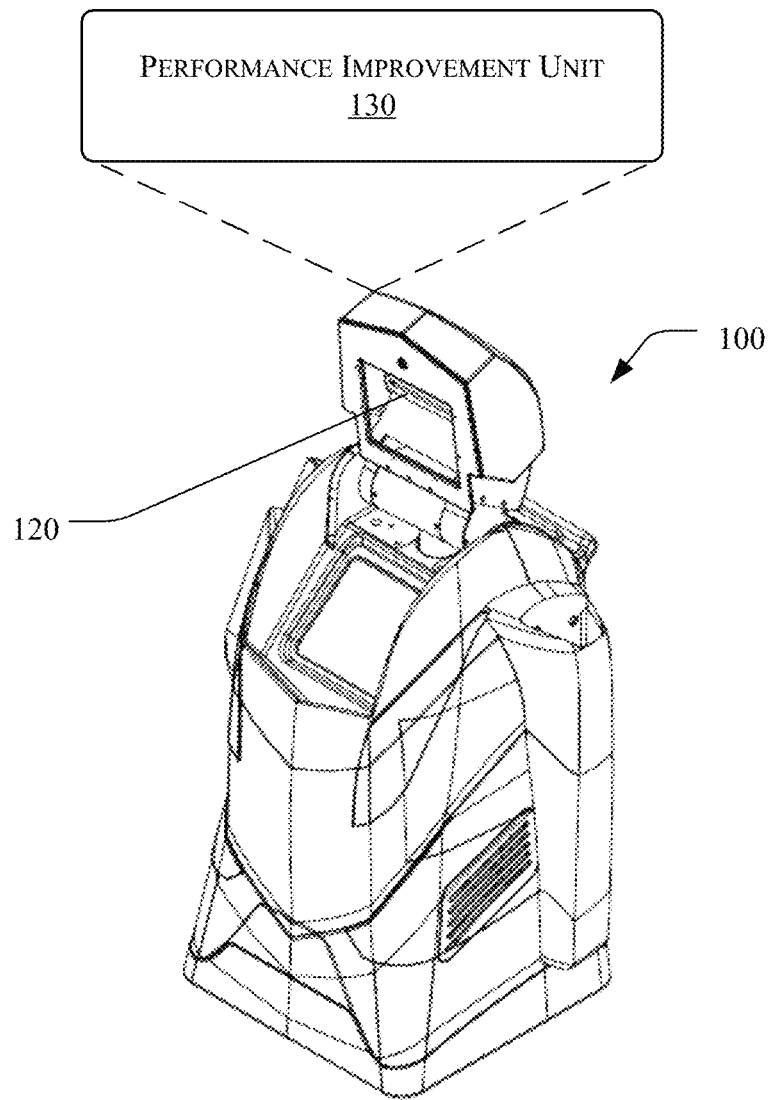
FIG. 1 illustrates a PUV device including an exemplary performance improvement unit according to an embodiment of the present disclosure.

The following detailed description is provided with reference to the figures. Exemplary embodiments are described to illustrate the disclosure, not to limit its scope, which is defined by the claims. Those of ordinary skill in the art will recognize number of equivalent variations in the description that follows without departing from the scope and spirit of the disclosure.

Non-Limiting Definitions

Definitions of one or more terms that will be used in this disclosure are described below without limitations. For a person skilled in the art, it is understood that the definitions are provided just for the sake of clarity and are intended to include more examples than just provided below.

"Disinfection" is used in the present disclosure within the context of its broadest definition. The disinfection may refer to any process or technique of inactivating or killing contaminants including cancerous cells, tumorous tissues, and/or pathogens on a target surface using the UV light alone or in combination with a variety of biocompatible agents known in the art, related art, or developed later including, but not limited to, chemical agents (e.g., alcohols, oxidizing agents, naturally occurring or modified compounds, etc.), physical agents (e.g., heat, pressure, vibration, sound, radiation, plasma, electricity, etc.), and biological agents (e.g., living organisms, plants or plant products, organic residues, etc.).

A "pulsed-ultraviolet (PUV) disinfection device" or "PUV device" is used in the present disclosure within the context of its broadest definition. The PUV device may refer to a standalone or a networked electronic or electromechanical device capable of providing pulses of UV light of a predetermined energy within a germicidal wavelength range of the electromagnetic spectrum for disinfection.

"Current Rating" is used in the present disclosure within the context of its broadest definition. The current rating may refer to a maximum current that a device, or a circuit therewith, can carry for a set period before manipulating or interrupting a current flow therethrough, or becoming unfunctional, under predefined operating conditions including, but not limited to, temperature and resistance of the device, or any component or circuit electrically or magnetically coupled thereto.

"Voltage Rating" is used in the present disclosure within the context of its broadest definition. The voltage rating may refer to a maximum voltage that a device, or a component or circuit therewith, can bear before failing to perform a designated or intended function under predefined operating conditions including, but not limited to, temperature, resistance, and current through the device, the component, or a circuit being electrically or magnetically coupled thereto.

"Cut-off current" is used in the present disclosure within the context of its broadest definition. The cut-off current may refer to a value of input current being substantially restricted, or negligibly conducted, through a component, or a circuit coupled therewith. In some embodiments, the cut-off current may include or depend on the current rating of a device, e.g., a circuit breaker.

"Operational performance," or any aspects thereof, is used in the present disclosure within the context of its broadest definition. The operational performance may refer to an ability of a device to incessantly provide a set amount of intended output or result for a predefined duration. In one example, the operational performance of the PUV device may refer to its ability to incessantly provide a set amount of germicidal light for a predefined duration sufficient to disinfect a set of one or more target surfaces. In some embodiments, the operational performance may be defined in terms of an electrical performance and/or disinfection performance of the PUV device.

"Electrical performance," or any aspects thereof, is used in the present disclosure within the context of its broadest definition. The electrical performance may refer to an ability of the PUV device to withstand changes in electrical parameters (e.g., current, voltage, etc.) during operation for a predefined duration.

"Disinfection performance," or any aspects thereof, is used in the present disclosure within the context of its broadest definition. The disinfection performance may refer to an ability of the PUV device to disinfect a set of one or more target surfaces within a predefined duration.

Exemplary Embodiments

FIG. 1 illustrates a PUV device 100 including an exemplary performance improvement unit 130 according to an embodiment of the present disclosure. Embodiments and concepts disclosed herein are described in the context of a room or area disinfection device; however, one having ordinary skill in the art would understand that such embodiments and others may be implemented with any suitable electrical, electronic, or electromechanical systems, devices, or components capable of generating pulses of energy for various purposes including, but not limited to, disinfection, communication, signal processing, and data storage.

The PUV device 100 of the present disclosure may represent a wide variety of devices configured to emit or facilitate emission of pulsed-UV light of a predetermined energy within a germicidal wavelength range (e.g., 100 nm to 400 nm, 180 nm to 350 nm, 100 nm to 1000 nm, etc.) of the electromagnetic spectrum. In one embodiment, as shown in FIG. 1, the PUV device 100 may be configured as a room or area disinfection device including a UV lamp 120 configured to emit PUV light having predetermined characteristics (e.g., intensity, frequency, power, wavelength, etc.) suitable to disinfect a target surface in a short period (e.g., approximately 10 minutes or less) from a relatively long distance (e.g., at least approximately 1 meter or more from the target surface). The UV lamp 120 may be of any suitable type known in the art, related art, or developed later including a mercury-vapour UV lamp, a Xenon UV lamp, and so on. The UV lamp 120 may be a pulsed radiation source, a continuous radiation source, or a set of both the pulsed radiation and the continuous radiation sources. The pulsed radiation source may be configured for emitting pulses of UV light within a predefined or dynamically defined germicidal wavelength range. The pulsed radiation source may be configured to have a pulse frequency, pulse width, pulse duration, or duty cycle that may cause the emitted PUV light to appear as continuous to a human eye. On the other hand, the continuous radiation source may be configured for being turned on and off at a predetermined frequency to emit pulses of UV light. In some embodiments, the UV lamp 120 may be configured for being flexible and diverge or converge the emitted PUV light. In some other embodiments, the UV lamp 120 may be coupled physically or wirelessly to the PUV device 100 or any portion thereof. Other embodiments may include the UV lamp 120 being a set of one or more UV lamps.

Embodiments of the PUV device 100, or a portion thereof (e.g., a UV unit or assembly), may be configured as a fixed, mobile, or handheld unit including one or more types of light sources such as a visible light source and an infrared light source. Some embodiments may include the PUV device 100 or any portions thereof being automated or configured to move, navigate, and/or operate autonomously. These portions may include the entire PUV device 100 or its sub-portions including, but not limited to, a lamp assembly, a support assembly, a remote unit, a control unit, a set of actuators or mobility devices, utility pods, one or more cooling systems, and a power unit. Such portions may be configured to move (e.g., pan, swivel, rotate, tilt, oscillate, pivot, extend, etc.) or navigate independently or relative to another portion, a component, an axis/plane of the PUV device 100, an object proximate to the PUV device 100, or a stimulus. Some other embodiments may include the PUV device 100 being configured to operate independently or in communication with a set of one or more devices including, but not limited to, (i) sensors (e.g., motion sensors or proximity sensors; temperature sensors; light sensors such as infrared sensors, UV sensors, and visible-light sensors; sound sensors such as ultrasonic sensors; vibration sensors; pathogen detection sensors; pathogen identification sensors; altimeter; pedometer; magnetometer; ozone sensors; smoke sensors; electrical parameter sensors such as voltage sensors, current sensors, power sensors, dose/dosage sensors, and intensity sensors, etc.), (ii) remote control devices (e.g., wired or wireless devices, portable or fixed devices, dedicated or smart devices, generic or application-specific devices, scanners or readers, servers or client devices, automated or non-automated, machine-controlled or user-controlled devices, single-use or multi-use devices, etc.), (iii) another disinfection apparatus (e.g., a light-based disinfection apparatus, a chemical disinfection apparatus, a sound or vibration-based disinfection apparatus, liquid or vapour-based disinfection apparatus, etc.), (iv) autonomous and non-autonomous devices, (v) robotic or non-robotic devices, and/or any components (including implementing or supporting computer programs) connected or supported therewith.

Other embodiments may include the PUV device 100 having video, voice, or data communication capabilities (e.g., unified communication capabilities) either independently or in communication with one or more network devices by being coupled to or including, various imaging devices (e.g., cameras, printers, scanners, medical imaging systems, etc.), various audio devices (e.g., microphones, music players, recorders, audio input devices, speakers, audio output devices, telephones, speaker telephones, etc.), various video devices (e.g., monitors, projectors, displays, televisions, video output devices, video input devices, camcorders, etc.), or any other type of hardware, in any combination thereof. The PUV device 100 may comprise or implement one or more real time protocols (e.g., session initiation protocol (SIP), H.261, H.263, H.264, H.323, etc.) and non-real-time protocols known in the art, related art, or developed later to facilitate data transfer to and from the network device. The PUV device 100 may also include a variety of known, related art, or later developed interface(s), including software interfaces (e.g., an application programming interface, a graphical user interface, etc.); hardware interfaces (e.g., cable connectors, a keyboard, a card reader, a barcode reader, a biometric scanner, an interactive display screen, a printer, sensors, etc.); or both. The interface(s) may facilitate communication over a network (not shown) between various components or network devices coupled to the PUV device 100.

When room or large area UV disinfection is desired, an operator may devoid human occupancy in the designated area where the disinfection is to be performed prior to activating the PUV device 100 to avoid health hazards due to the PUV light emitted by the UV lamp 120. The PUV device 100 may be activated for a predefined or dynamically defined period (hereinafter also referred to as a disinfection cycle) and may be interrupted either on-demand by the operator or based on preset or dynamically set conditions such as those indicated by various sensors (e.g., motion/vibration sensors, occupancy/proximity sensors, ozone sensors, temperature sensors, smoke sensors, pathogen level detection sensors, etc.) in communication with the PUV device 100. Examples of these conditions may include, but not limited to, motion detection in the proximity of the PUV device 100 or by remote sensors communicating therewith, temperature of a radiation source such as the UV lamp 120 above a predefined threshold, an accumulation of ozone above a predefined threshold, and so on.

In one exemplary embodiment, the PUV device 100 may include a performance improvement unit 130 configured to, at least one of, (1) generate a pulsed-output signal 212 comprising of one or more trigger pulses (e.g., voltage pulses, current pulses, etc.) for driving a component/device such as the UV lamp 120; (2) provide the pulsed-output signal 212 at a constant voltage relative to an operating voltage of such component/device; (3) manipulate an input current across the PUV device 100, or a component thereof (e.g., a circuit breaker 204, discussed below in detail) based on one or more characteristics (e.g., frequency, pulse width, pulse duration, duty cycle, time period, etc.) of the pulsed-output signal 212; (4) configure the pulsed-output signal 212 to adjust the input current for being below a cut-off input current (or cut-off current) associated with the circuit breaker 204; (5) modulate one or more of the characteristics for driving the pulsed-output signal 212 with at least two distinct pulse frequencies per second (hereinafter interchangeably referred to as compound frequencies) for a predefined or dynamically defined operational period (e.g., disinfection cycle); (6) select or adjust at least one frequency in the compound frequencies for being greater than a predefined cut-off frequency associated with the pulsed-output signal 212, where the cut-off frequency may correspond to the cut-off current that may trip or deactivate the circuit breaker 204 and in turn shut down the component/device (e.g., the UV lamp 120) driven by the pulsed-output signal 212; (7) select or adjust at least one frequency in the compound frequencies for being less than the cut-off frequency of the pulsed-output signal 212; (8) drive the pulsed-output signal 212 with the compound frequencies including a first frequency being greater than or equal to the cut-off frequency and a second frequency being less than the cut-off frequency; (9) manipulate an intensity of PUV light generated by the UV lamp 120 upon being driven by the pulsed-output signal 212 at the compound frequencies; and (10) prevent or delay turning-off the PUV device 100, or the UV lamp 120 connected thereto, while increasing the intensity of PUV light generated therefrom.

The performance improvement unit 130 may be implemented as a standalone and dedicated device including hardware and installed software, where the hardware may be closely matched to the requirements and/or functionality of the software; however, in some embodiments, the performance improvement unit 130 may be implemented as a combination of multiple devices that are operatively connected or networked together. In some other embodiments, the performance improvement unit 130 may be a hardware device including processor(s) executing machine readable program instructions, which may be stored on a computer readable medium, and installed or embedded in an appropriate device for execution. Generally, the computer or machine executable instructions may include routines, programs, objects, components, data structures, procedures, modules, functions, and the like that may perform particular functions or implement particular abstract data types.

The processor(s) may include, for example, microprocessors, microcomputers, microcontrollers, digital signal processors, central processing units, state machines, logic circuits, and/or any devices that manipulate signals based on operational instructions. Among other capabilities, the processor(s) may be configured to fetch and execute computer readable instructions in a dedicated or shared memory associated with the performance improvement unit 130 for performing tasks such as signal coding or encoding, signal or data processing, input/output processing, voltage, current, or power control, and/or other functions. The "hardware"

may comprise a combination of discrete components, an integrated circuit, an application-specific integrated circuit, a field programmable gate array, a digital signal processor, or other suitable hardware. The "software" may comprise one or more objects, agents, threads, lines of code, subroutines, separate software applications, two or more lines of code or other suitable software structures operating in one or more software applications or on one or more processors.

In one or more embodiments, the performance improvement unit 130 may include a telemetry circuit to communicate with any of a variety of computing devices (e.g., a desktop PC, a personal digital assistant (PDA), a server, a mainframe computer, a mobile computing device (e.g., mobile phones, laptops, etc.), an internet appliance, etc.). In some other embodiments, the performance improvement unit 130 may operate, cease to operate, or perform any predefined alternate function, in response to a portable device or a wearable device including, but not limited to, a fashion accessory (e.g., a wrist band, a ring, etc.), a utility device (e.g., a hand-held carry-case, a pen or stylus, a body monitor, a timing device, etc.), a body clothing, or any combinations thereof. In some embodiments, the performance improvement unit 130 may enhance or increase the functionality and/or capacity of the network to which it may be connected. The performance improvement unit 130 of some embodiments may include software, firmware, or other resources that support remote administration, operation, and/or maintenance of the PUV device 100.

Figure 2:
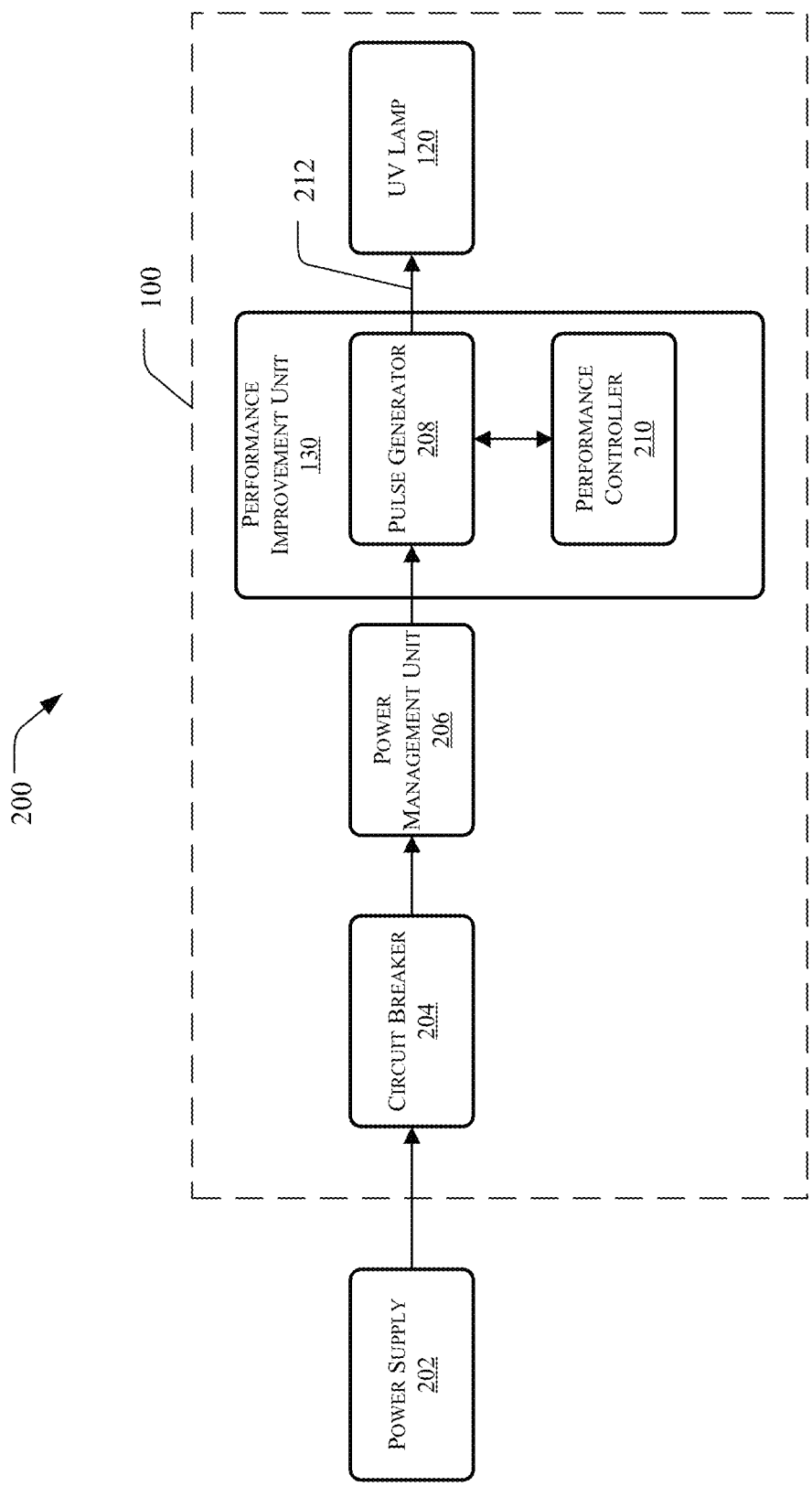
FIG. 2 is an exemplary schematic of a PUV system including the performance improvement unit of FIG. 1 according to an embodiment of the present disclosure.

FIG. 2 is an exemplary schematic of a PUV system including the performance improvement unit 130 of FIG. 1 according to an embodiment of the present disclosure. Embodiments of the PUV system 200 may include fewer, more, or different components in a variety of configurations including those disclosed herein. A skilled artisan would understand that these components may communicate in a cohesive or distributed manner or may be disposed on one or more carriers such as circuit boards and integrated circuits in communication with the performance improvement unit 130.

In one embodiment, the PUV system 200 may include a power supply 202 in electrical communication with the PUV device 100 including the performance improvement unit 130. The power supply 202 may include any type of suitable voltage source known in the art, related art, or developed later including a primary battery, a rechargeable or secondary battery, or the mains power supply 202 suitable or configurable to electrically power the PUV device 100. Examples of the power supply 202 may include, but not limited to, metal-based or mineral-based batteries, super capacitors, nuclear or atomic batteries, mechanical resonators, infrared collectors, thermally-powered energy sources, flexural-powered energy sources, bioenergy power sources, fuel cells, bioelectric cells, and osmotic pressure pumps, or any combinations thereof.

In one or more embodiments, the power supply 202 may supply a high-voltage or an alternating current (AC) power signal to the PUV device 100 for operation. The power supply 202 may be electrically coupled to the PUV device 100 either physically or wirelessly using any of a variety of mechanisms known in the art. For example, the power supply 202 may be a battery being supported with the PUV device 100. In another example, the power supply 202 may include a capacitor bank operatively coupled to the PUV device 100. The capacitor bank may be powered by another power source, e.g., a mains power supply or a battery. In yet another example, the power supply 202 may include a distributed power system including a charging coil and a power coil configured for being inductively coupled thereto. The charging coil may be electrically coupled to a power source such as a mains power supply 202 or a battery, and positioned outside the PUV device 100. The power coil may be configured to inductively receive electromagnetic power from the charging coil based on the power coil being arranged within a coverage area of the charging coil and/or at a predefined angle or orientation therewith. One having ordinary skill in the art would understand various components and aspects thereof to implement the distributed power system. Examples of these aspects may include, but are not limited to, (i) respective coverage areas, quality factors, and coupling coefficients of the coils, (ii) an intended range of charging, (iii) an angle, orientation, and/or distance between the coils, and (iv) a resonant frequency of the coils. Further, the power supply 202 may apply a set voltage (e.g., 110V) to the PUV device 100. In some embodiments, the power supply 202 or aspects thereof may be positioned on the PUV device 100.

In one embodiment, the PUV device 100 may include a circuit breaker 204, a power management unit 206, the UV lamp 120, and the performance improvement unit 130. However, in some embodiments, the PUV device 100 may additionally include a power adaptor (not shown) configured to adapt the voltage (e.g., 110 V) provided by the power supply 202 to a different voltage configuration (e.g., 220 V) depending on a load complexity and/or circuit compatibility of the PUV device 100.

The circuit breaker 204 may operate as an electrical gateway between the power supply 202 and the PUV device 100, or any particular portions thereof. The circuit breaker 204 may include any suitable electrical switching device configured to interrupt an input current therethrough relative to a cut-off current defining a safe current limit for the PUV device 100. The cut-off current may be defined relative to a preset current rating of the circuit breaker 204 depending on a configuration thereof. For example, a resettable, multiuse circuit breaker 204 may be configured with a cut-off current being less than the preset current rating. Another example may include a single-use circuit breaker 204 configured with a cut-off current being equal to the preset current rating thereof. In one embodiment, the circuit breaker 204 may regulate a flow of power signal delivering the input current, e.g., from the power supply 202, to the PUV device 100, or any components or blocks thereof. The circuit breaker 204 may trip or deactivate to interrupt the power signal based on the input current across the circuit breaker 204 becoming unsafe "overcurrent" by reaching or exceeding the cut-off current. A skilled artisan would understand to implement any suitable type of circuit breaker 204 known in the art, related art, or developed later depending on an installation location, a design, an interrupting mechanism, a voltage applied across the circuit breaker 204, or any other aspects thereof. Examples of these aspects include, but are not limited to, single-use or resettable/multiuse configurations, automatic and/or manual operability, arrangement and number of active elements (e.g., transistors, diodes, integrated circuits, etc.) and/or passive elements (e.g., resistors, capacitors, inductors, etc.), and temperature and/or current sensitivity.

The circuit breaker 204 may be adapted to operate in tandem or communicate with any suitable component of the PUV device 100. In one embodiment, as illustrated, the circuit breaker 204 may be coupled with the power management unit 206 of the PUV device 100. The power management unit 206 may be configured to manipulate electrical aspects (e.g., voltage level, current level, signal conversion, etc.) of the power signal received through the circuit breaker 204 before being applied to different electrical components of the PUV device 100. For example, the power management unit 206 may include a rectifier (not shown) to convert an alternating current (AC) power signal received from the power supply 202 via the circuit breaker 204 to a direct current (DC) power signal. The rectifier may be configured as a half-wave, full-wave, single phase, multiphase, or any other suitable configuration known in the art, related art, or developed later depending on a component being fed with the power signal. In some embodiments, the DC power signal may have a voltage level same as that of the corresponding AC power signal; however, one having skill in the art would understand that a voltage of the DC power signal may differ from that of the corresponding AC power signal depending on the electrical component being driven. In another example, the power management unit 206 may additionally include a voltage transformer (not shown) configured to adjust a voltage of the power signal to an output voltage relative to an operating voltage of an intended component of the PUV device 100. The voltage transformer may have any suitable configurations known in the art, related art, or developed later including, but not limited to, a step-up voltage transformer, a step-down voltage transformer, or a combination thereof. For instance, the voltage transformer may increase an input voltage of the power signal to an output voltage compliant with the operating voltage to power the UV lamp 120. In another instance, the voltage transformer may drive the power signal with an output voltage sufficient to trigger the UV lamp 120 for a PUV operation. The power signal having the output voltage, or an adjusted voltage, may be fed forward for driving the performance improvement unit 130.

The performance improvement unit 130 may be configured to generate a pulsed-output signal 212 for driving an intended component such as the UV lamp 120. The performance improvement unit 130 may include a pulse generator 208 and a performance controller 210, one or each of those may be coupled to a processor(s) and a computer memory. The pulse generator 208 may be configured to generate the pulsed-output signal 212 for driving the UV lamp 120 to emit PUV light having predefined characteristics (e.g., energy, power, wavelength, frequency, etc.) according to an intended application, and a distance between the UV lamp 120 and a target surface. For example, the pulsed-output signal 212 may drive the UV lamp 120 to emit 10 to 1500 Joules of energy per pulse of UV light within a predefined frequency range from 1-50 Hz for a distance of approximately 1 to approximately 3 meters between the UV lamp 120 and a target surface for disinfection; however, a skilled artisan may contemplate other suitable frequency ranges including, but not limited to, 1 Hz to 50 Hz, 10 Hz to 28 Hz, 10 Hz to 40 Hz, 20 Hz to 50 Hz, and 15 Hz to 40 Hz. Other suitable characteristics may be contemplated for effective disinfection at greater distances from the target surface. A skilled artisan would understand other aspects (e.g., operational period, temperature, etc.) of the pulse generator 208 to drive the UV lamp 120 for intended applications including, but not limited to, disinfection, communication, signal processing, and data storage.

The pulse generator 208 may be configured to trigger or drive a UV lamp such as the UV lamp 120 with the pulsed-output signal 212 having a predefined number of pulses per second, i.e., pulse frequency. The number of pulses applied per second to the UV lamp 120 may be increased to improve a UV output of the UV lamp 120 and hence, the disinfection performance. However, an increase in the number of pulses per second or the pulse frequency, in general, also increases the input current applied across the PUV device 100, particularly the circuit breaker 204. The relationship between the pulse frequency and the input current can be understood based on an input power provided by the power signal received from the power supply 202 via the circuit breaker 204 and an output power delivered by the pulsed-output signal 212 generated by the pulse generator 208.

During operation, the power supply 202 may provide the power signal at a preset supply voltage (e.g., 110V) to the PUV device 100 via the circuit breaker 204. The power signal may deliver the input current across the circuit breaker 204 and pass therethrough to the power management unit 206. The input power delivered by the power signal across the circuit breaker 204, and the PUV device 100, may be represented by Equation 1.

$$P_{in} = V_{in} \cdot I_{in} \qquad (1)$$

where: $P_{in}$=Input power provided by the power signal received from the power supply
$V_{in}$=Input voltage applied across the circuit breaker by the power signal
$I_{in}$=Input current applied across the circuit breaker by the power signal The power management unit 206 may adjust a voltage of the received power signal based on a component of the PUV device 100 to be driven by the power signal. For example, the power management unit 206 may adjust the voltage of the power signal to generate an adjusted power signal at a constant voltage (e.g., 2000V) compliant with an operating voltage of the UV lamp 120. The voltage-adjusted power signal may be received by the pulse generator 208, which may include a set of capacitors (not shown). The adjusted power signal may charge the capacitors that may discharge to generate one or more pulses of energy, which may be delivered as the pulsed-output signal 212. Each energy pulse of the pulsed-output signal 212 within an operational period (e.g., a disinfection cycle) may deliver an output power represented by Equation 2. The number of pulses generated per second, or a portion thereof, may define a pulse frequency associated with the pulsed-output signal 212, as represented by Equation 3.

$$P_{out} = \frac{E_o}{T_o} \qquad (2)$$

where: $P_o$=Output power delivered by the pulsed-output signal
$E_o$=Energy delivered by the pulsed-output signal, where $$E_o = \frac{1}{2} \cdot C \cdot V_o^2$$

C=Total capacitance of all capacitors associated with the pulse generator
$T_o$=Operational period for which the energy $E_o$ is delivered $$F_o = \frac{1}{T_o} \qquad (3)$$

where: $F_o$=Pulse frequency or no. of pulses per second of the pulsed-output signal generated during the operational period $T_o$ Based on Equations 2 and 3, the output power of pulsed-output signal 212 may be a factor of the pulse frequency thereof, represented in Equation 4.

$$P_{out} = E_o \cdot F_o \quad (4)$$

Since a set of one or more capacitors in the pulse generator 208 may be charged by the power signal, the output power delivered by the pulsed-output signal 212 may be proportional to an input power provided by the power signal, as represented in Equation (5).

$$\Rightarrow P_{in} \propto P_o \quad (5)$$

$$\Rightarrow V_{in} \cdot I_{in} \propto E_o \cdot F_o \quad (6)$$

$$\Rightarrow V_{in} \cdot I_{in} \propto \frac{1}{2} \cdot C \cdot V_o^2 \cdot F_o \quad (7)$$

$$\Rightarrow I_{in} \propto F_o \quad (8)$$

Figure 4A:
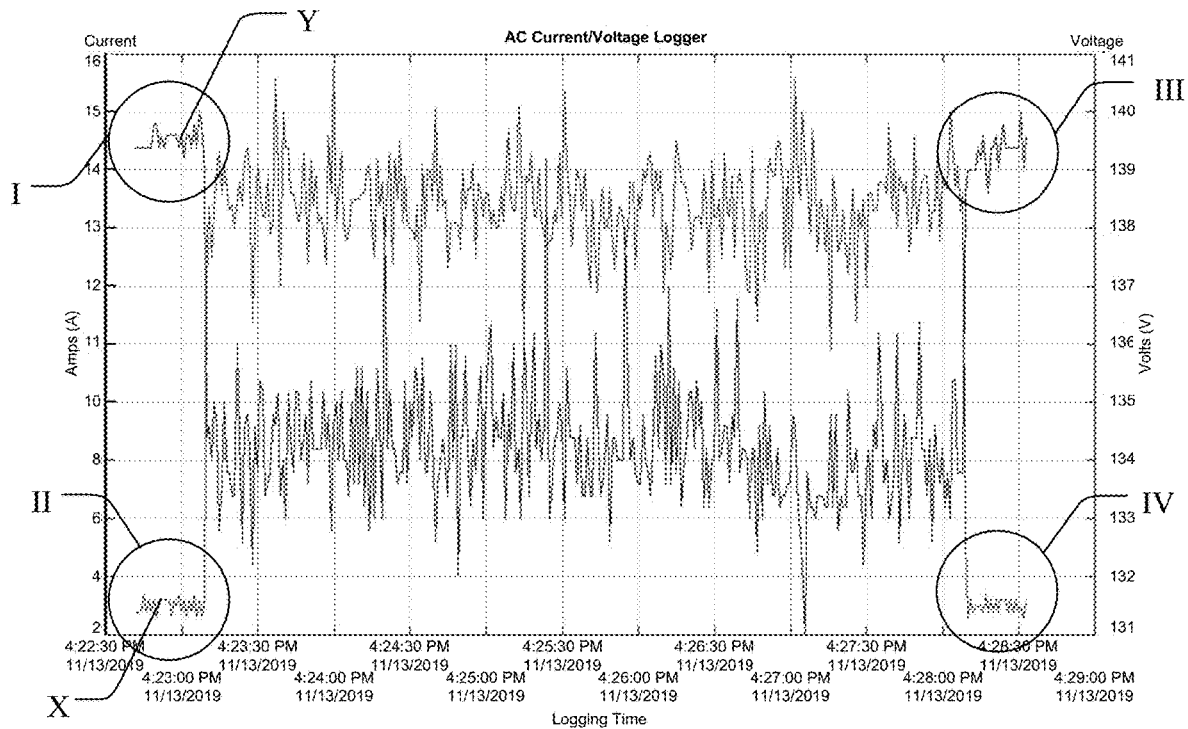
FIGS. 4A-4B, 5A-5C, 6A-6C, and 7A-7B are typical graphs of test results indicating voltages and currents across a circuit breaker of the PUV device of FIG. 2 upon being driven by a pulsed signal at different fixed frequencies.
Figure 4B:
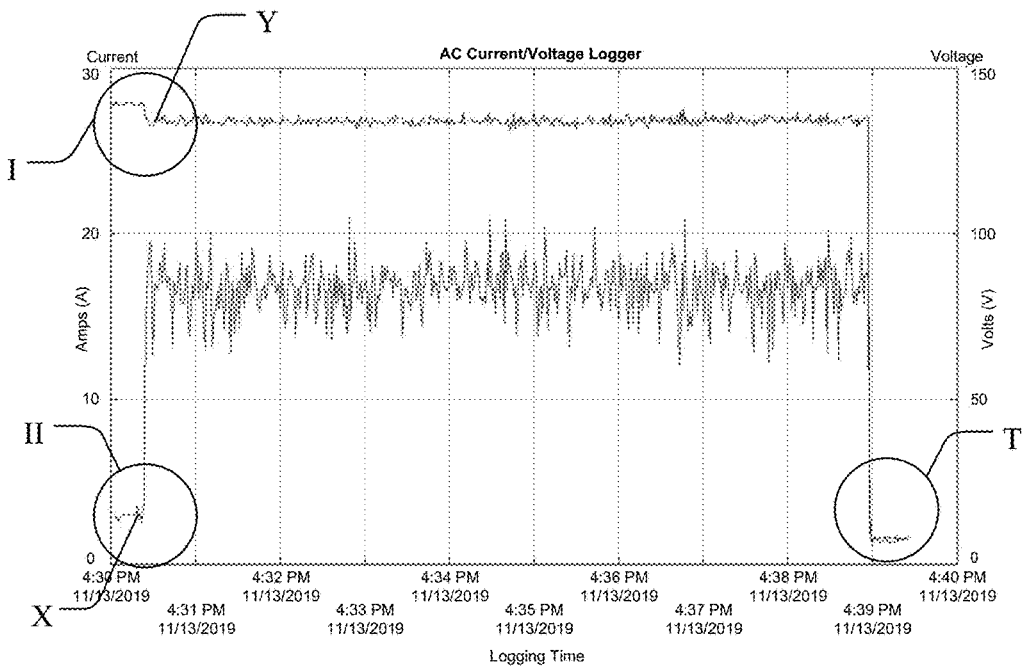

Based on Equations 5-8, the input current $I_{in}$ may be directly proportional to the pulse frequency $F_o$ of pulsed-output signal 212. Any increase in the pulse frequency $F_o$ may cause an increase in the input current $I_{in}$ across the circuit breaker 204. The pulse frequency $F_o$ that may cause the input current $I_{in}$ to exceed the cut-off current and trip the circuit breaker 204, may be referred to as the cut-off frequency $F_{cut}$. For example, as shown in FIGS. 4A-4B, which illustrate graphs of test results indicating voltages and currents across the circuit breaker 204 upon being driven by the pulsed-output signal 212 at a fixed or set frequency of 29 Hz. The FIGS. 4A-4B indicate the voltage and current changes caused across the circuit breaker 204 by the pulsed-output signal 212 at 29 Hz for operational durations of 5 minutes and 10 minutes respectively.

In FIGS. 4A-4B, electrical parameter values are indicated along the y-axis and the operational durations are indicated along the x-axis. The graphs also include a curve X (red lines) and a curve Y (blue lines) indicating the input current and the voltage across the circuit breaker 204 respectively during a predefined operational period. The current values for the curve X are indicated on the left y-axis and the voltage values for the curve Y are indicated on the right y-axis.

At an outset of the operational duration of 5 minutes, the FIG. 4A indicates that at point I, the voltage across the circuit breaker 204 averages at 138V, which is indicative of a supply voltage of 118V with a voltage correction factor of 20V during operation. At the same instant, at point II, the input current across the circuit breaker 204 averages at less than 3 Amp, which is indicative of an applied current of less than 1 Amp with a current correction factor of 15 Amp. During operation, the voltage drops and averages at 135V, which is indicative of 115V with the voltage correction factor. However, the current increases and averages at 17 Amp, which is indicative of 2 Amp with the current correction factor. The rise and fall in the curves X and Y are due to charging and discharging of capacitors in the pulse generator 208 to generate the pulsed-output signal 212 which may affect the input current across the circuit breaker 204 based on the above Equation 8. At the end of the operational period of 5 minutes, the pulse generator 208 stops generating the pulsed-output signal 212 for driving the UV lamp 120. As a result, the voltage (indicated by curve Y) across the circuit breaker 204 goes back to average at 138V, indicative of a supply voltage of 118V (with the voltage correction factor) across the circuit breaker 204 at point III. Similarly, the current (indicated by curve X) drops back to being less than 3 Amp, which is indicative of an applied current of less than 1 Amp (with the current correction factor) at point IV. Since the voltage and current go back to the starting levels only after the end of the operational duration, it may indicate that the pulse generator 208 generates the pulsed-output signal 212 at the set frequency of 29 Hz to successfully drive the UV lamp 120 for 5 minutes without tripping the circuit breaker 204.

On the other hand, the FIG. 4B indicates that the voltage (indicated by curve Y) averages at 118V (at point I) and the current (indicated by curve X) averages being less than 1 Amp (at point II) with the respective correction factors at the outset of the operational period of 10 minutes. However, both the voltage (indicated by curve Y) and the current (indicated by curve X) drop unexpectedly before the end of the operational period. As shown, before the end of 10 minutes, the voltage drops to near-zero volts and the input current drops to less than 1 Amp (at point T) with the respective correction factors. Such unexpected drop in the voltage and current before the end of 10 minutes indicates that the circuit breaker 204 being tripped. Therefore, the FIGS. 4A-4B establish that 29 Hz may be the cut-off frequency associated with the pulsed-output signal 212 for driving the cut-off current across the circuit breaker 204 during operation.

Figure 5A:
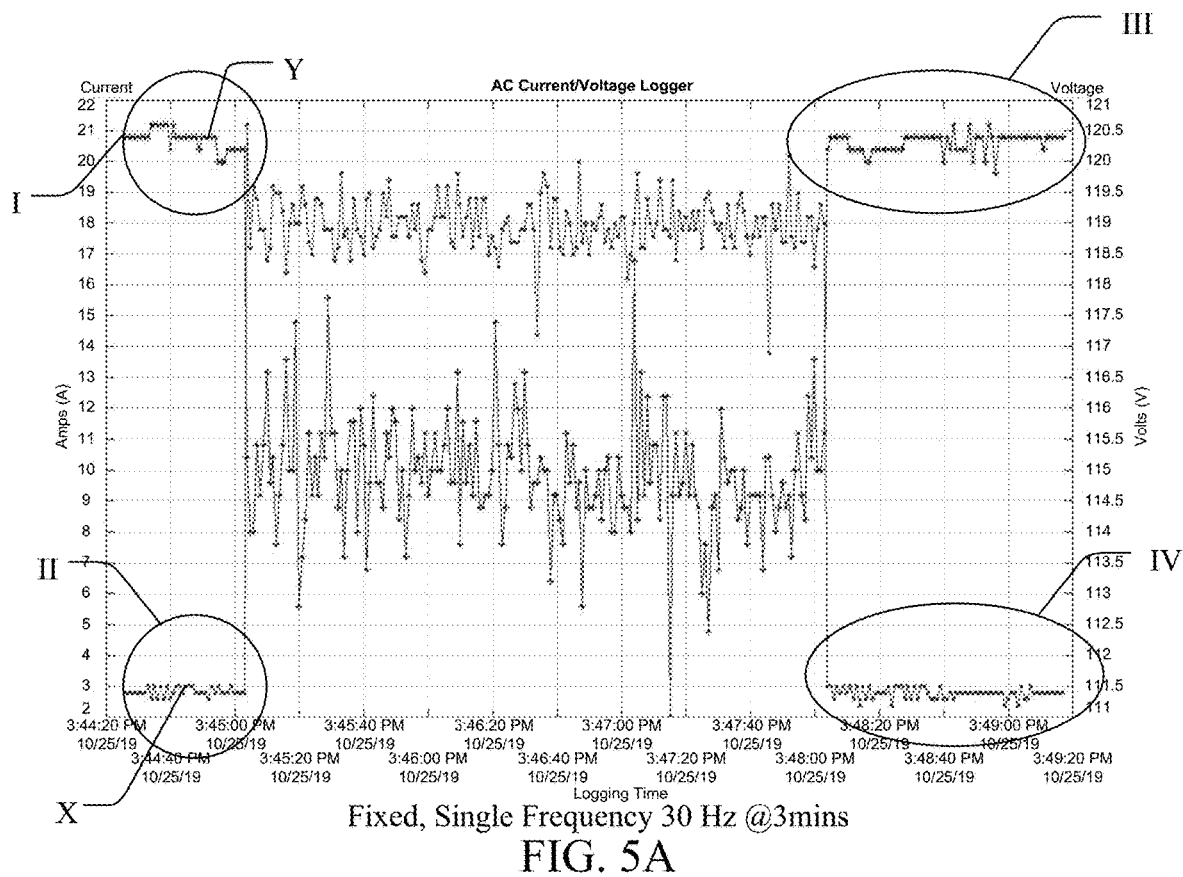

It may also be noted that pulsed-output signal 212 operated at any frequency greater than the cut-off frequency may continue to trip the circuit breaker 204. This is established in FIGS. 5A-5C and 6A-6C which illustrate graphs of test results indicating voltages and currents across the circuit breaker 204 upon being driven by the pulsed signal at a fixed or set frequency of 30 Hz and 33 Hz respectively. Particularly, the FIGS. 5A-5C indicate the voltage and current changes caused across the circuit breaker 204 by the pulsed-output signal 212 at 30 Hz for operational durations of 3 minutes, 5 minutes, and 10 minutes respectively. FIGS. 6A-6C indicate the voltage and current changes caused across the circuit breaker 204 by the pulsed-output signal 212 at 33 Hz for operational durations of 3 minutes, 5 minutes and 10 minutes respectively.

In FIGS. 5A-5C and 6A-6C, electrical parameter values are indicated along the y-axis and the operational durations are indicated along the x-axis. The graphs also show the curve X (red lines) and the curve Y (blue lines) indicating the input current and the voltage across the circuit breaker 204 respectively during respective predefined operational periods. The current values for the curve X are indicated on the left y-axis and the voltage values for the curve Y are indicated on the right y-axis.

Figure 5B:
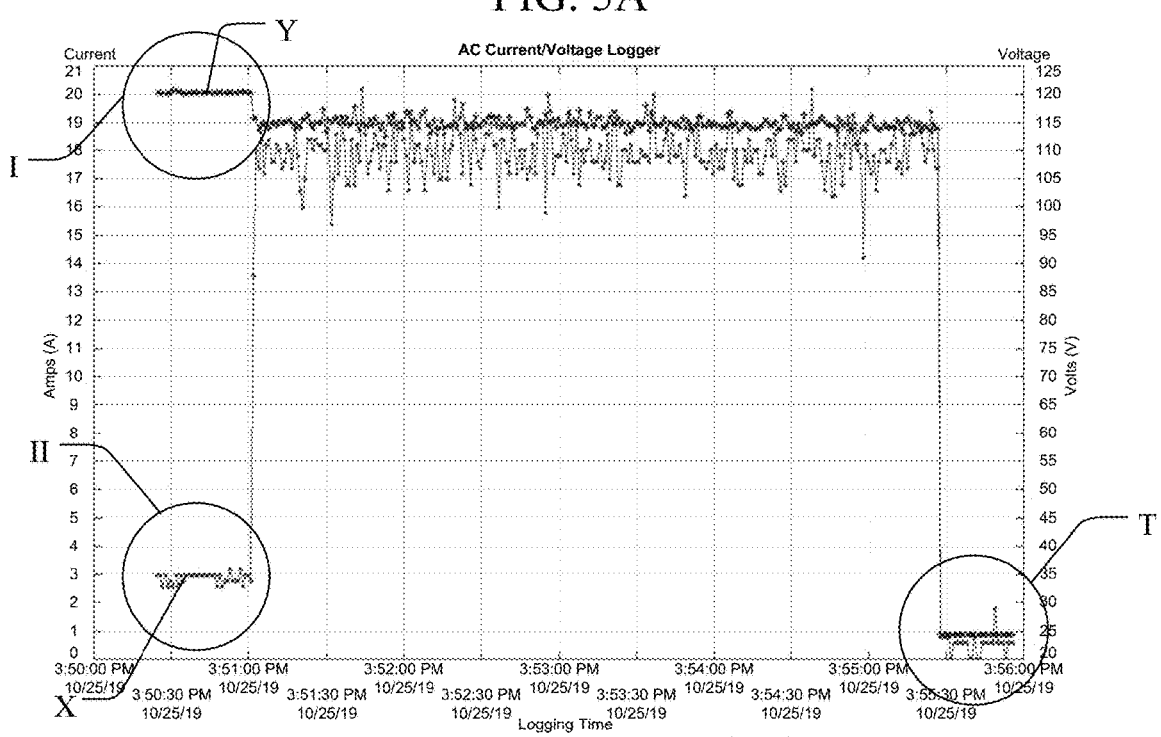
Figure 5C:
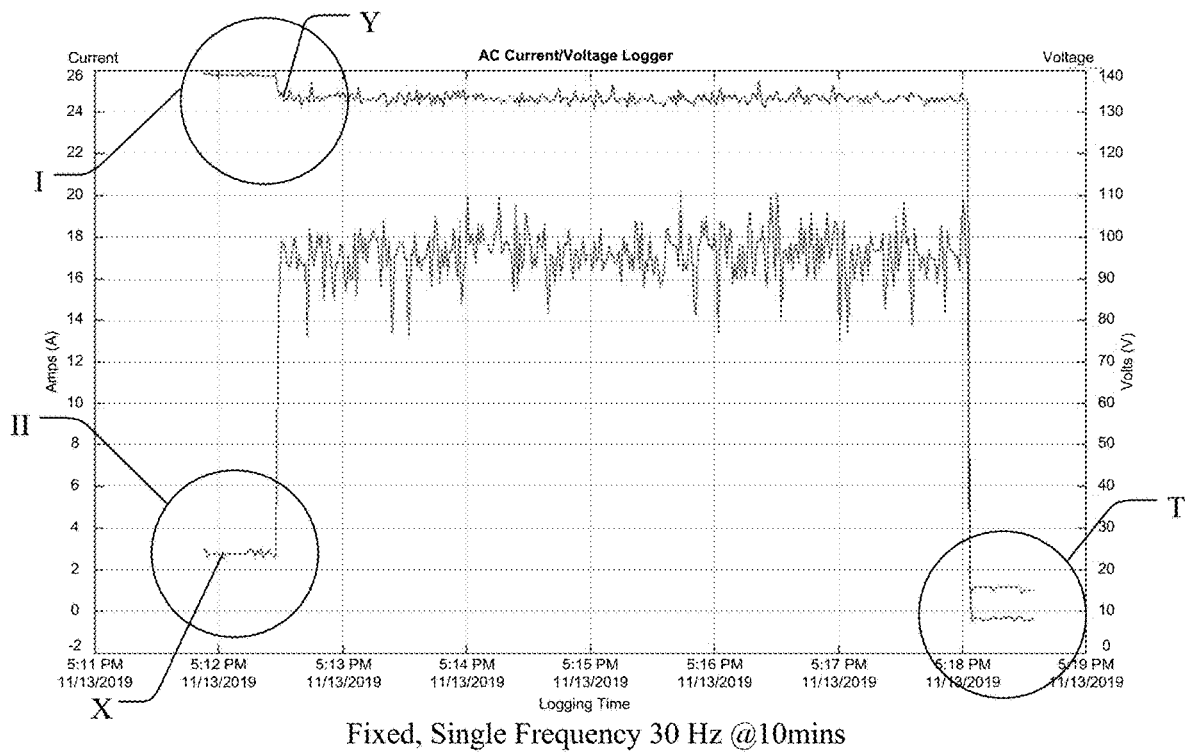
Figure 6A:
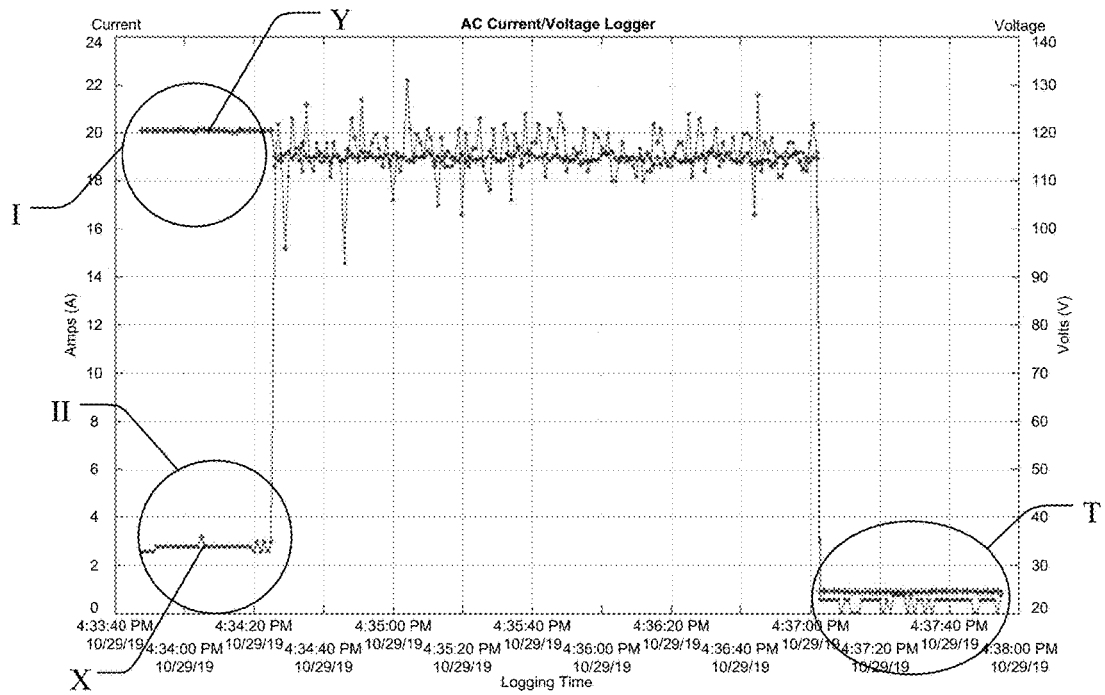
Figure 6B:
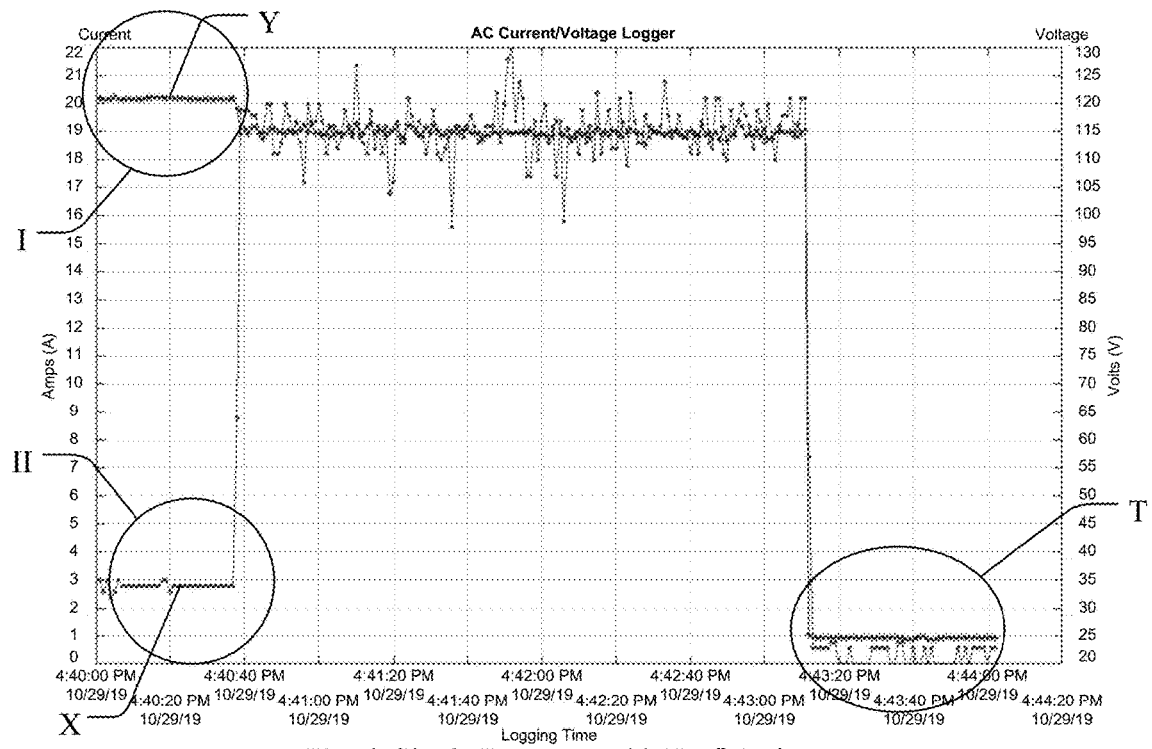
Figure 6C:
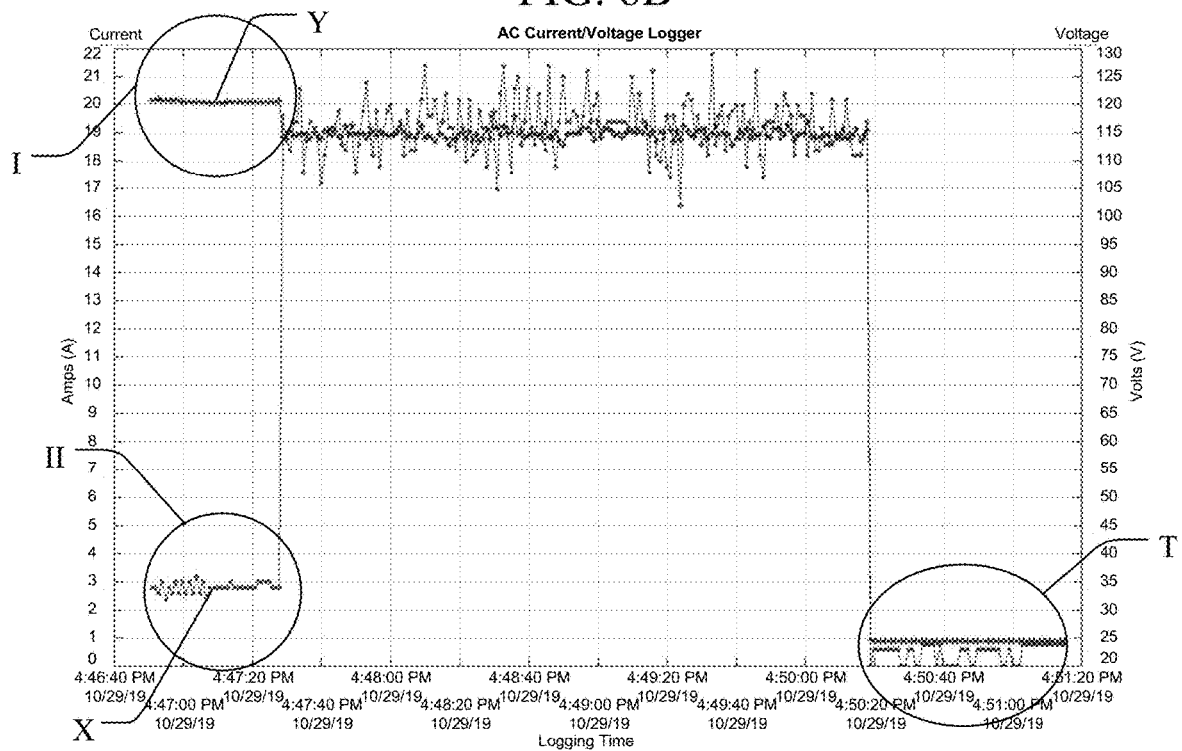

As shown in FIGS. 5B-5C, similar to FIG. 4B, both the voltage (indicated by curve Y) and the current (indicated by curve X) drop unexpectedly before the end of respective operational periods. As shown, in FIGS. 5A-5C, the voltage (indicated by curve Y) drops to near-zero volts and the input current (indicated by curve X) drops to less than 1 Amp (at point T) with the respective correction factors 20V and 15 Amp before the end of 5 minutes and 10 minutes respectively. Such unexpected drops in the voltage and current before the end of operational periods degraded as compared to the pulsed-output signal 212 at the cut-off frequency of 29 Hz, and indicate the circuit breaker 204 being tripped even for a shorter duration of 5 minutes. Similarly, in FIGS. 6A-6C, the voltage (indicated by curve Y) drops to near-zero volts and the input current (indicated by curve X) also drops to less than 1 Amp (at point T) with the respective correction factors of 20V and 15 Amps before the end of 3 minutes, 5 minutes, and 10 minutes respectively. Such unexpected drops in the voltage and current before the end of operational periods worsened as compared to the pulsed-output signal 212 at the frequencies of 29 Hz and 30 Hz, and indicate the circuit breaker 204 being tripped for a further short duration of 3 minutes.

In one embodiment, the pulse generator 208 may be configured to, at least one of, (1) generate the pulsed-output signal 212 using the power signal received from the power management unit 206 via the circuit breaker 204, where the generated pulsed-output signal 212 may include one or more trigger pulses for driving a component of the PUV device 100 such as the UV lamp 120; (2) provide the pulsed-output signal 212 at a constant voltage being relative to an operating voltage of a component of PUV device 100 such as the UV lamp 120; (3) configure the pulsed-output signal 212 based on one or more control signals from the performance controller 210 to manipulate the input current across the circuit breaker 204 for being below the cut-off current and prevent the circuit breaker 204 from being tripped or deactivated; and (4) manipulate an intensity of PUV light generated by the UV lamp 120 upon being driven by the configured pulsed-output signal 212. In some embodiments, the constant voltage of the pulsed-output signal 212 may be adjusted by the pulse generator 208 to drive different types of UV sources (e.g., a low or high voltage UV lamps, a light emitting diode (LED), etc.). In some other embodiments, the pulse generator 208 may condition the pulsed-output signal 212 before being applied to a UV source such as the UV lamp 120. For example, the pulse generator 208 may condition the pulsed-output signal 212 to have one or more pulses with a desired shape such as square, rectangular, triangular, spikes, and so on. A skilled artisan would be able to contemplate any other suitable conditioning attributes of the pulsed-output signal 212 for being modified prior to driving a component such as the UV lamp 120.

The pulse generator 208 may be in signal communication with the performance controller 210, which may be configured to enable an interruption-free operation of the PUV device 100 while improving the performance thereof. The performance controller 210 may control one or more predefined or dynamically defined functions or aspects of the pulse generator 208. In one embodiment, the performance controller 210 may be configured to, at least one of, (1) define a threshold current being relatively less than the cut-off current of the circuit breaker 204 to provide a control signal; (2) determine a predetermined cut-off frequency of the pulsed-output signal 212 that increases a drawn input current to exceed the cut-off current and trip the circuit breaker 204; (3) provide one or more control signals to modulate one or more characteristics of the pulsed-output signal 212 for being driven with at least two distinct pulse frequencies per second (or compound frequencies) for a predefined or dynamically defined period ("operational period"); (4) determine at least one frequency for the compound frequencies from a predefined group of upper frequencies greater than the predetermined cut-off frequency associated with the pulsed-output signal 212; (5) determine at least one frequency for the compound frequencies from a predefined group of lower frequencies less than the predetermined cut-off frequency associated with the pulsed-output signal 212; (6) determine a predefined or dynamically defined operational period for which the one or more characteristics may be modulated for driving the pulsed-output signal 212 with the compound frequencies; (7) adjust or vary a combination of frequencies in the compound frequencies for maximizing an intensity of the UV light while preventing the circuit breaker 204 from being tripped based on the input current being manipulated to be less than the cut-off current; and (8) communicate the determined compound frequencies to the pulse generator 208 based on the one or more control signals.

In one embodiment, the performance controller 210 may be configured for controlling the pulse generator 208 to generate the pulsed-output signal 212 at compound frequencies for a predefined or dynamically defined operational period (e.g., disinfection cycle) and prevent the PUV device 100 being unintentionally interrupted during operation. The operational period may vary depending on an intended application (e.g., surface disinfection) of the PUV device 100 or the UV lamp 120 connected thereto. The compound frequencies may improve the electrical and disinfection performance of the PUV device 100 and prevent the circuit breaker 204 from being tripped due to the overcurrent.

Figure 3:
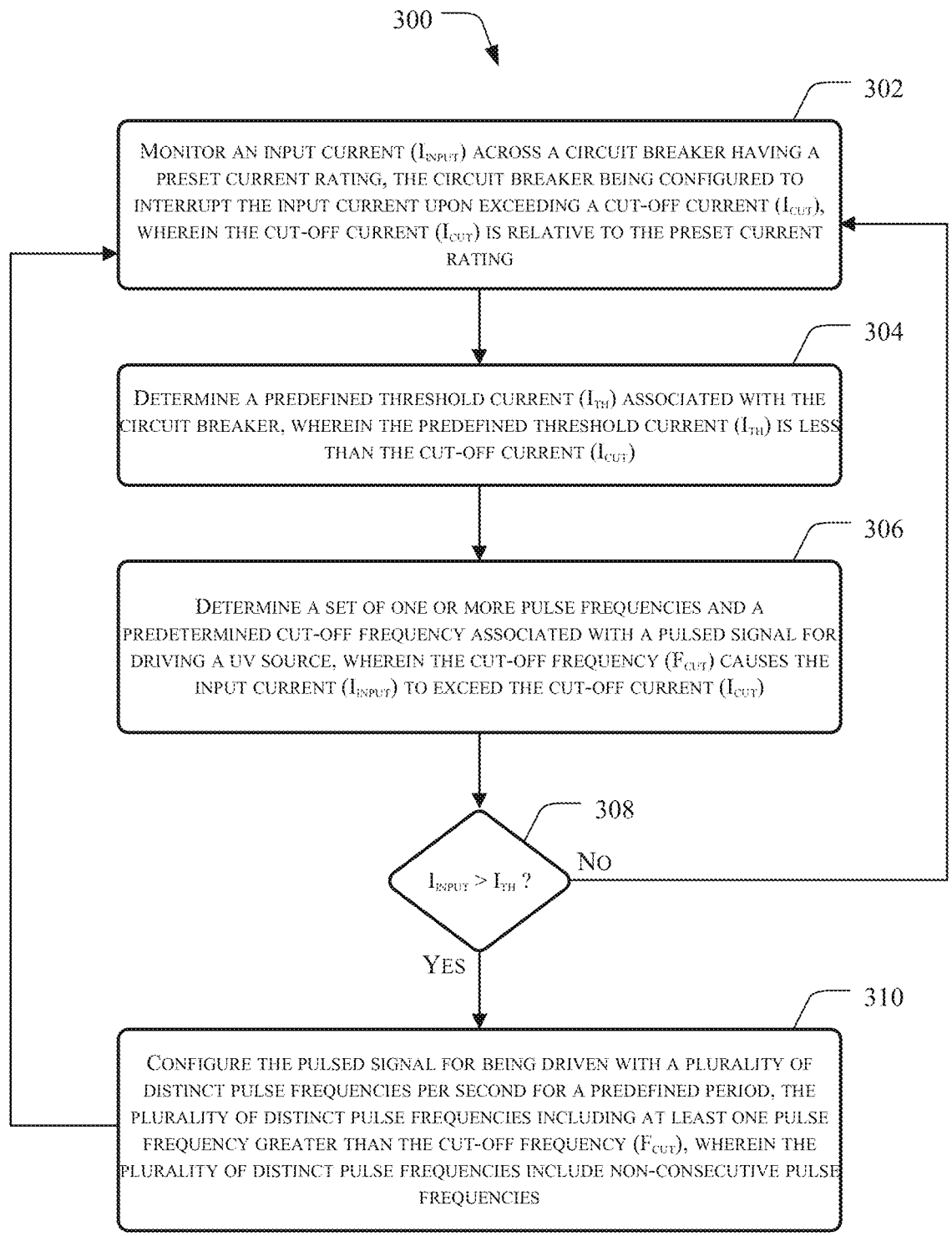
FIG. 3 is a flowchart illustrating an exemplary method for implementing the performance improvement unit of FIG. 1 according to an embodiment of the present disclosure.

FIG. 3 is a flowchart illustrating an exemplary method for implementing the performance improvement unit 130 of FIG. 1 according to an embodiment of the present disclosure. The order in which the method 300 is described is not intended to be construed as a limitation, and any number of the described method blocks may be combined, deleted, or otherwise performed in any order to implement the method 300 or an alternate method without departing from the scope and spirit of the present disclosure. The exemplary method 300 may be described in the general context of computer-executable instructions, which may be stored on a computer readable medium, and installed or embedded in an appropriate device for execution. Further, the method 300 may be implemented in any suitable hardware, software, firmware, or combination thereof, that exists in the related art or that is later developed.

In one embodiment, the method 300 may be implemented by the pulse generator 208. However, one having ordinary skill in the art would understand that aspects of the method 300 may be performed on the performance controller 210. At step 302, an input current across the circuit breaker 204 may be monitored. In one embodiment, the pulse generator 208 may monitor the input current across the circuit breaker 204 having a preset current rating. The circuit breaker 204 may be configured to interrupt the input current upon exceeding a cut-off current being relative to the preset current rating. The input current may be monitored using a variety of techniques known in the art, related art, or developed later. For example, the PUV device 100 may include a current sensor (not shown) electrically coupled to the circuit breaker 204 and the pulse generator 208. Upon being switched on or being actively coupled to the power supply 202, the PUV device 100 may initiate the current sensor in communication with the pulse generator 208 to assess the input current across the circuit breaker 204. The current sensor may provide a measure of input current delivered by the power signal across the circuit breaker 204. However, in some embodiments, the pulse generator 208 may directly monitor the input current by virtue of being electrically coupled to the circuit breaker 204.

In embodiments including a distributed arrangement for the PUV device 100, the pulse generator 208 may include a different configuration to monitor the input current across the circuit breaker 204. For example, the circuit breaker 204 and the power management unit 206 may be located on a first device wirelessly coupled with a second device including the performance improvement unit 130 and the UV lamp 120. The first device may be configured to wirelessly power the second device, e.g., through inductive coupling. In such scenario, the pulse generator 208 on the second device may wirelessly sense the input current across the circuit breaker 204 in the first device from the current sensor over a network. For example, the first device may include the current sensor and a respective module (not shown), which may enable the current sensor and/or the first device being introduced to a network appliance, thereby enabling the network appliance to invoke the current sensor and/or the first device as a service. Examples of the network appliance include, but are not limited to, a DSL modem, a wireless access point, a router, a base station, and a gateway. The network appliance may communicate the input current measured by the current sensor to the second device, or the pulse generator 208 therewith, over the network. The pulse generator 208 may be configured to monitor the input current in signal communication with the performance controller 210. In some embodiments, the input current across the circuit breaker 204 may be monitored by the performance controller 210 using the current sensor.

At step 304, a predefined threshold current associated with the circuit breaker 204 may be determined. In one embodiment, the pulse generator 208 may be configured with a threshold current for the circuit breaker 204. The threshold current may be predefined or dynamically defined by a user via a user interface or defined by the performance controller 210 based on a transition delay of the power signal while delivering the input current across the circuit breaker 204. A skilled artisan would understand any other aspects for the pulse generator 208 to automatically define the threshold current. In some embodiments, the pulse generator 208 may predefine a base threshold current that may be manipulated by a user for operation. The threshold current may be defined less than the cut-off current for enabling the pulse generator 208 to initiate configuring the pulse-output signal being generated therefrom in communication with the performance controller 210 and prevent the circuit breaker 204 from being tripped for the predefined operational period.

At step 306, a set of one or more pulses per second and a cut-off frequency associated with a pulsed signal is determined. The pulse generator 208 may be preconfigured in communication with the performance controller 210 to generate a pulse signal such as the pulsed-output signal 212 for driving the UV lamp 120. The pulsed-output signal 212 may include one or more pulses per second defining a pulse frequency thereof. In one embodiment, the pulse generator 208 may determine a set of one or more pulse frequencies associated with the pulsed-output signal 212. For example, the pulsed-output signal 212 may be configured with a set frequency (e.g., 20 pulses per second or 20 Hz) within a predefined frequency range (e.g., 1 Hz to 50 Hz). Another example may include the pulsed-output signal 212 being configured with multiple set frequencies (e.g., 20 pulses per second for the first 60 seconds, followed by 10 pulses per second for the remaining operational period) within the predefined frequency range. Further, the pulse generator 208 may be configured to determine a predetermined cut-off frequency associated with the pulsed-output signal 212. Since a frequency of the pulsed-output signal 212 may be proportional to the input current across the circuit breaker 204 based on Equation 8, any increase in such frequency may also increase the input current. Depending on a preset current rating of the circuit breaker 204, the frequency (i.e., cut-off frequency) at which the pulsed-output signal 212 causes the input current to exceed the cut-off current and trip the circuit breaker 204, may be predetermined and stored in a memory (not shown) associated with the PUV device 100 or the performance improvement unit 130 (e.g., with the pulse generator 208 or the performance controller 210). During operation, the pulse generator 208 may access the memory and determine the cut-off frequency associated with the pulsed-output signal 212.

At step 308, the input current across the circuit breaker 204 and the predefined threshold current may be compared. In one embodiment, the pulse generator 208 may generate the pulsed-output signal 212 at a preset pulse frequency. Based on the pulsed-output signal 212, the pulse generator 208 may check and compare the input current across the circuit breaker 204 with the predefined threshold current. For example, the pulse generator 208 may be configured to determine whether or not the input current exceeds the predefined threshold current. For a given frequency of the generated pulsed-output signal 212, the pulse generator 208 may be configured to execute a step 310 if the input current exceeds the predefined threshold current, else may continue to monitor the input current across the circuit breaker 204 at step 302.

At step 310, the pulsed-output signal 212 may be configured with multiple distinct pulse frequencies per second for a predefined period. In one embodiment, unlike the typical one frequency of pulses per second, the pulse generator 208 may configure the pulsed-output signal 212 with multiple distinct pulse frequencies per second (or compound frequencies) based on a corresponding input current exceeding the predefined threshold current. In one example, for each second within a predefined period (e.g., an operational period such as a disinfection cycle), the pulse generator 208 may add a new frequency or adjust an existing frequency of the pulsed-output signal 212 for being configured with the compound frequencies; however, another example may include the predefined period being shorter than the operational period or the disinfection cycle. The compound frequencies may include two or more distinct pulse frequencies belonging to any suitable frequency range depending on the cut-off frequency. For example, the compound frequencies may range from 1 Hz to 50 Hz for a cut-off frequency of 29 Hz; however, other suitable frequency ranges may be contemplated including those having an upper frequency greater than 50 Hz.

Figure 7A:
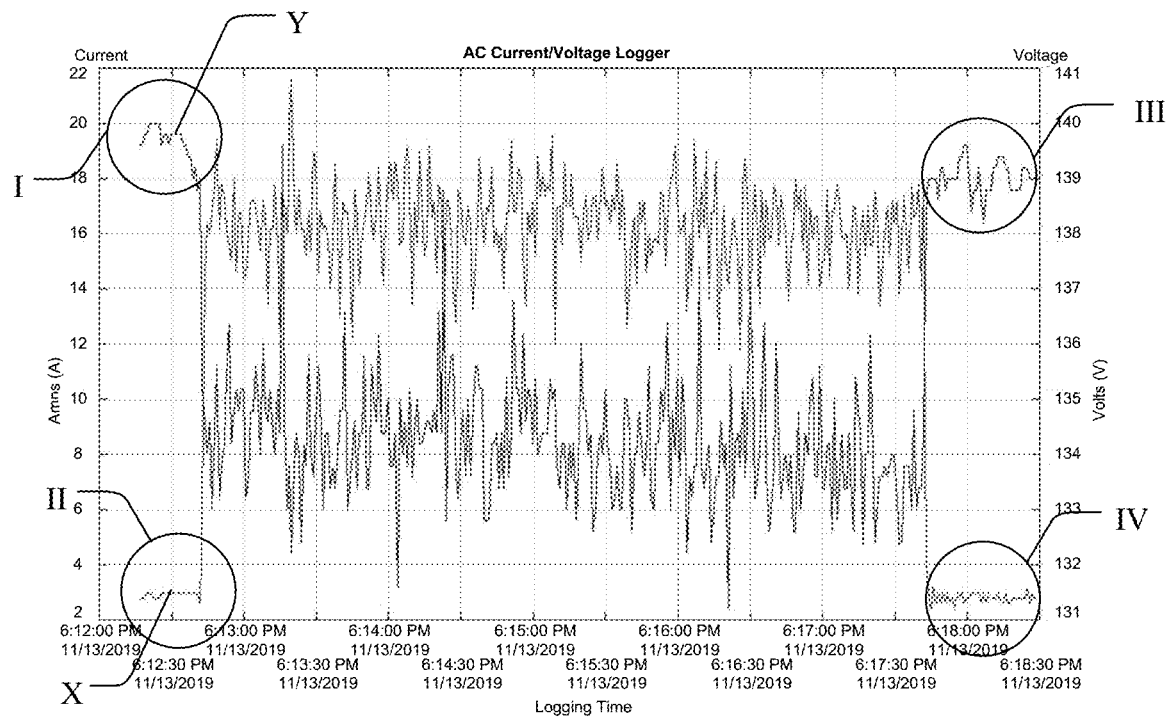
Figure 7B:
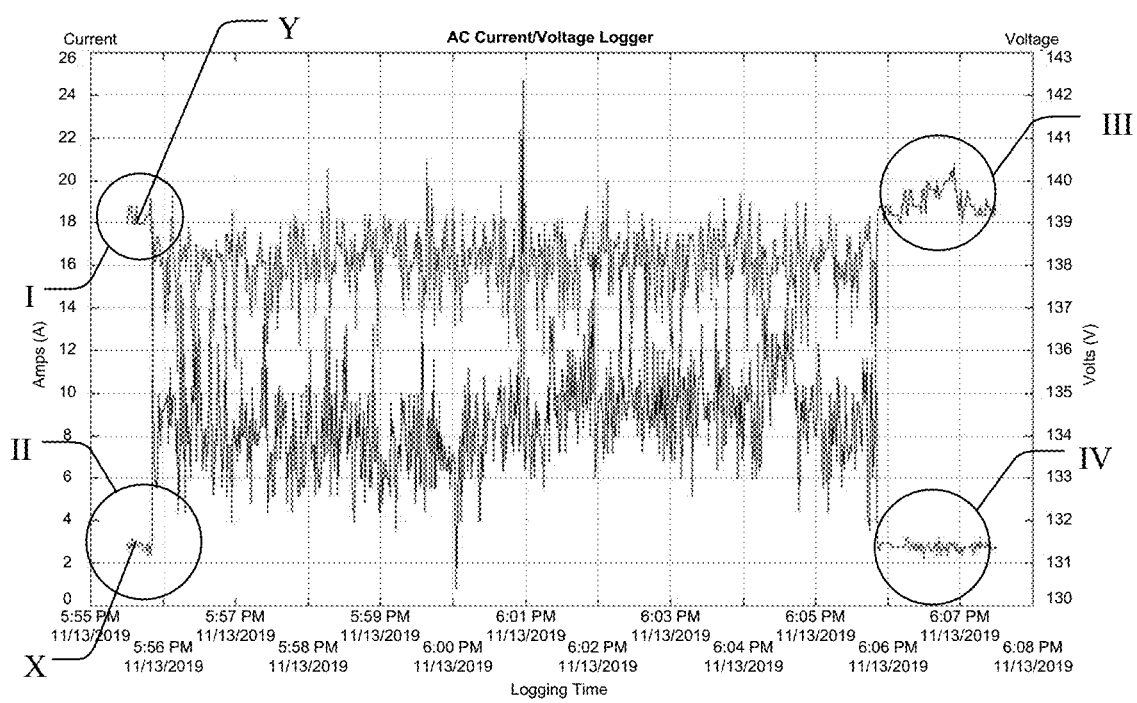
Figure 8A:
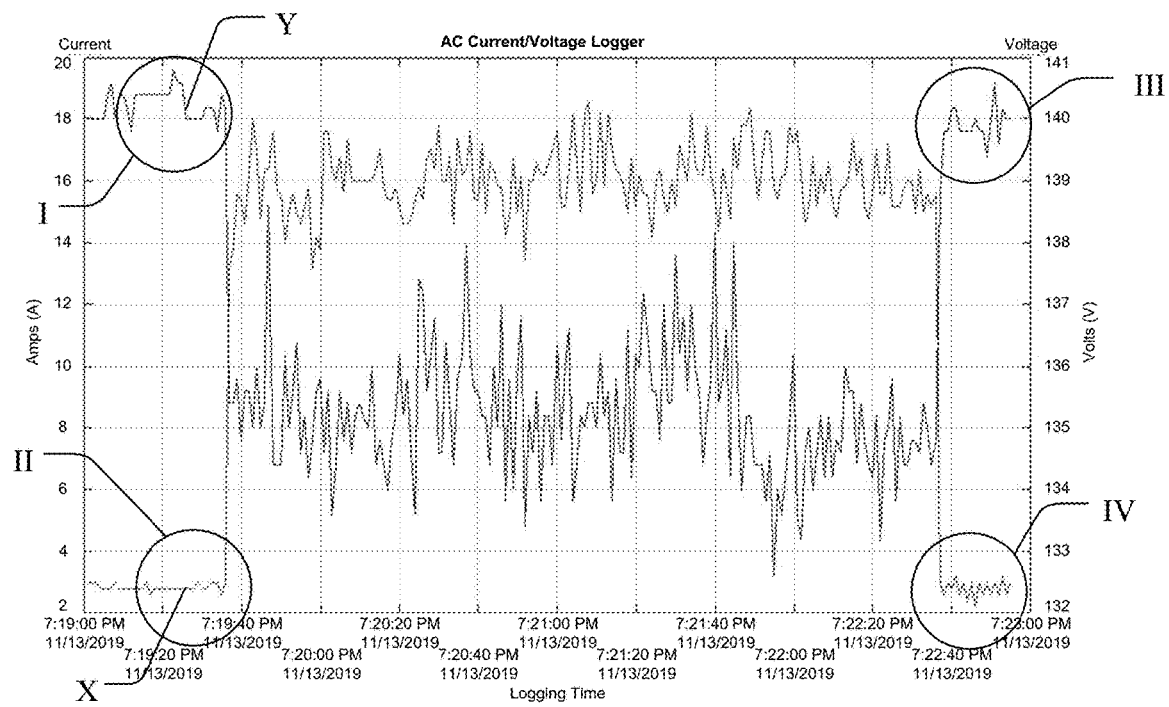
FIGS. 8A-8C and 9A-9C are exemplary graphs of test results illustrating voltages and currents across the circuit breaker of the PUV device of FIG. 2 upon being regulated by the performance improvement unit of FIG. 1 according to an embodiment of the present disclosure.
Figure 8B:
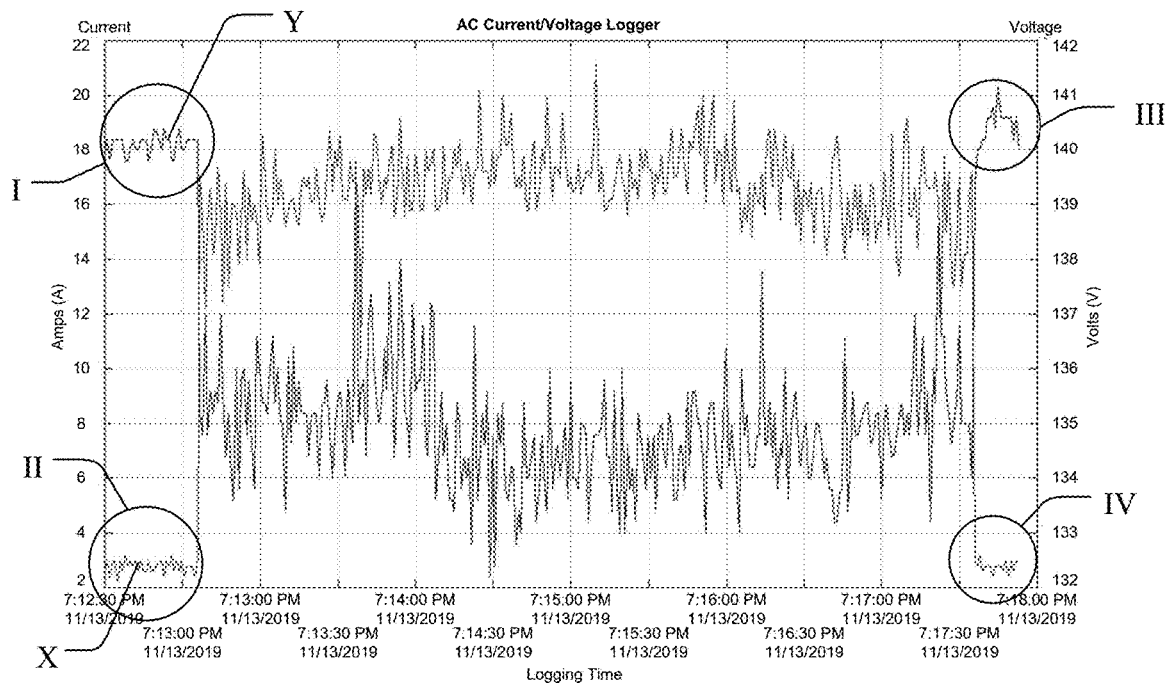
Figure 8C:
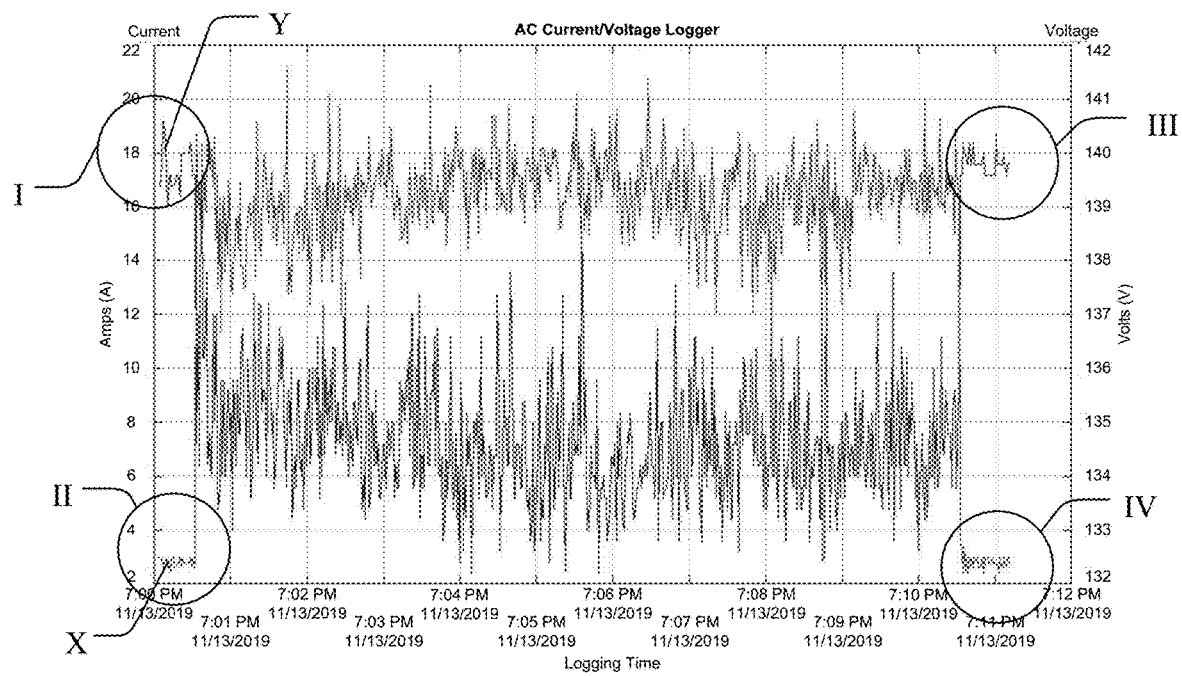
Figure 9A:
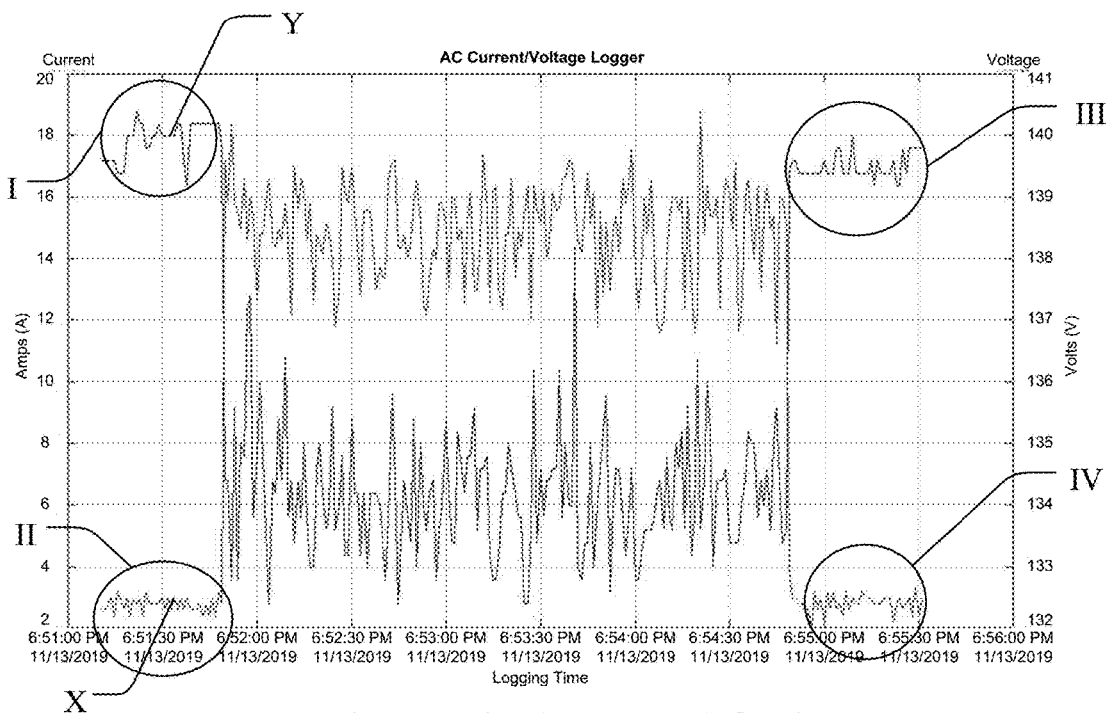
Figure 9B:
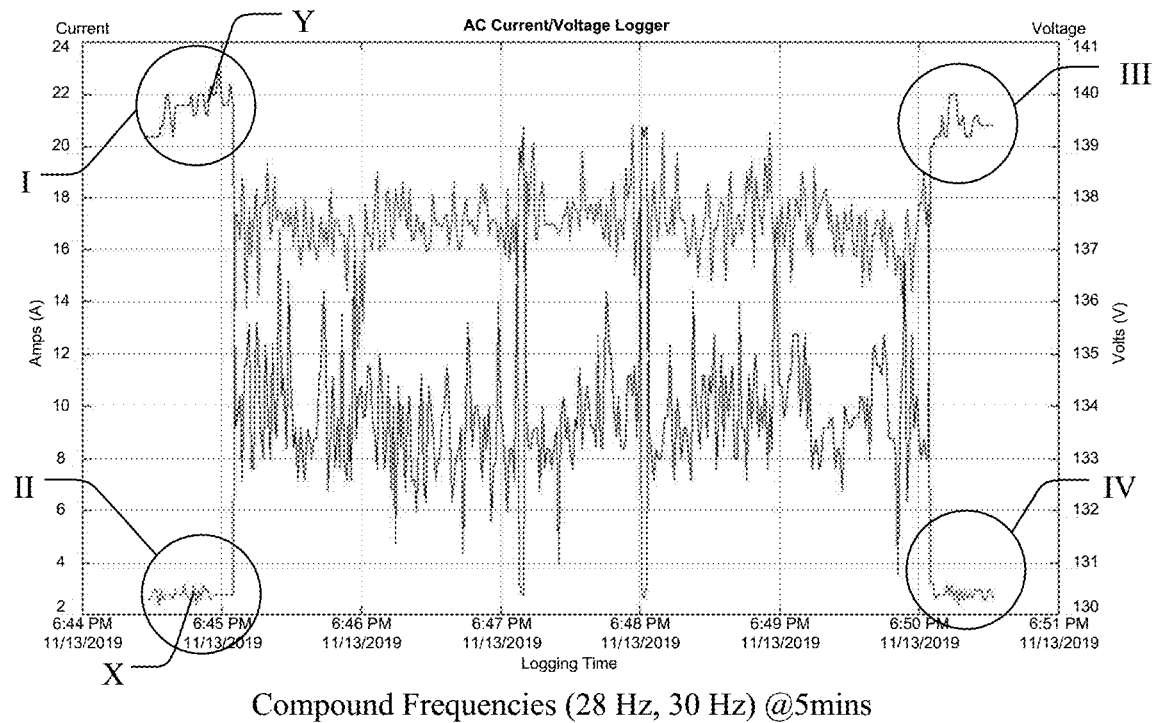
Figure 9C:
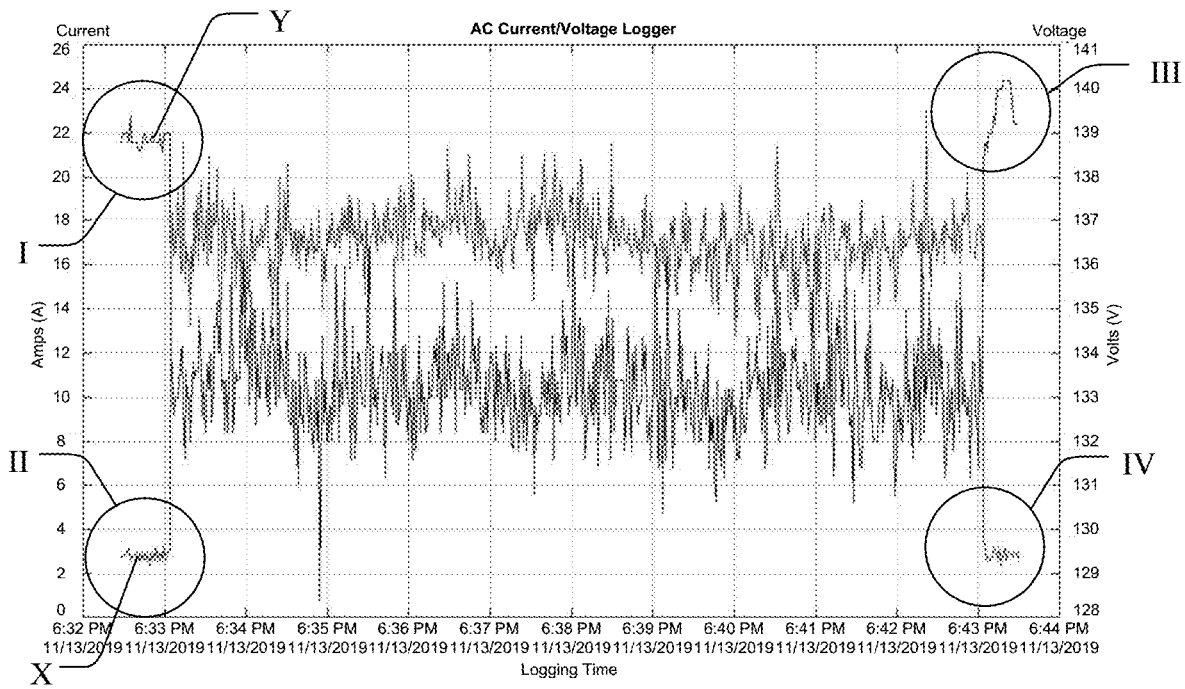

In one embodiment, the pulse generator 208 may include at least one frequency in the compound frequencies being greater than or equal to the cut-off frequency to maximize the UV output of the UV lamp 120. For example, the pulse generator 208 may generate the pulsed-output signal 212 at a set pulse frequency of 28 Hz for different operational periods or disinfection cycles such as 5 minutes and 10 minutes as shown in FIGS. 7A-7B, and may be associated with a cut-off frequency of 29 Hz as shown in FIGS. 4A-4B. FIGS. 7A-7B illustrate graphs of test results indicating voltages and currents across the circuit breaker 204 upon being driven by the pulsed signal at a fixed or set frequency of 28 Hz. Particularly, the FIGS. 7A-7B indicate the voltage and current changes caused across the circuit breaker 204 by the pulsed-output signal 212 at 28 Hz for operational durations of 5 minutes and 10 minutes respectively. In FIGS. 7A-7B, electrical parameter values are indicated along the y-axis and the operational durations are indicated along the x-axis. The graphs also include a curve X (red lines) and a curve Y (blue lines) indicating the input current and the voltage across the circuit breaker 204 respectively during a predefined operational period. The current values for the curve X are indicated on the left y-axis and the voltage values for the curve Y are indicated on the right y-axis. The rise and fall in the curves X and Y may be due to charging and discharging of capacitors in the pulse generator 208 to generate the pulsed-output signal 212 which may affect the input current across the circuit breaker 204 based on the above Equation 8. For both the operational durations 5 minutes and 10 minutes shown in the FIGS. 7A-7B respectively, the pulsed-output signal 212 successfully drives the UV lamp 120 without tripping the circuit breaker 204, as indicated by the voltage (indicated by curve Y) and the current (indicated by curve X) across the circuit breaker 204 going back to the near-starting levels only after the end of the operational durations, similar to that shown in FIG. 4A.

In one embodiment, the pulse generator 208 may configure the pulsed-output signal 212 with the compound frequencies including at least one frequency being equal to or greater than the cut-off frequency such as 29 Hz. For example, as shown in FIGS. 8A-8C and FIGS. 9A-9C, which illustrate exemplary graphs of test results depicting voltages and currents across the circuit breaker 204 upon being regulated by the performance improvement unit 130. In FIGS. 8A-8C and FIGS. 9A-9C, electrical parameter values are indicated along the y-axis and the operational durations are indicated along the x-axis. The graphs also include a curve X (red lines) and a curve Y (blue lines) indicating the input current and the voltage across the circuit breaker 204 respectively during a predefined operational period. The current values for the curve X are indicated on the left y-axis and the voltage values for the curve Y are indicated on the right y-axis. The rise and fall in the curves X and Y are due to charging and discharging of capacitors in the pulse generator 208 to generate the pulsed-output signal 212 which may affect the input current across the circuit breaker 204 based on the above Equation 8.

In a first example, the compound frequencies may include at least one frequency in the compound frequency being equal to the cut-off frequency, e.g., 29 Hz, provided at least one other frequency, e.g., 28 Hz, in the compound frequencies may be less than the cut-off frequency. The FIGS. 8A-8C indicate the voltage and current changes caused across the circuit breaker 204 by the pulsed-output signal 212 at compound frequencies of 28 Hz, 29 Hz per second for operational durations of 3 minutes, 5 minutes, and 10 minutes respectively. For each of the operational durations 3 minutes, 5 minutes, and 10 minutes shown in the FIGS. 8A-8C respectively, the pulsed-output signal 212 successfully drives the UV lamp 120 without tripping the circuit breaker 204, as indicated by the voltage (indicated by curve Y) and the current (indicated by curve X) across the circuit breaker 204 going back to the near-starting levels only after the end of the operational durations at points III and IV respectively.

In a second example, the compound frequencies may include at least one frequency, e.g., 30 Hz, in the compound frequency being greater than the cut-off frequency, e.g., 29 Hz, provided at least one other frequency, e.g., 28 Hz, in the compound frequencies may be less than the cut-off frequency. Similar to FIGS. 8A-8C, the FIGS. 9A-9C indicate the voltage and current changes caused across the circuit breaker 204 by the pulsed-output signal 212 at compound frequencies of 28 Hz, 30 Hz per second for operational durations of 3 minutes, 5 minutes, and 10 minutes respectively. For each of the operational durations 3 minutes, 5 minutes, and 10 minutes shown in the FIGS. 9A-9C respectively, the pulsed-output signal 212 successfully drives the UV lamp 120 without tripping the circuit breaker 204, as indicated by the voltage (indicated by curve Y) and the current (indicated by curve X) across the circuit breaker 204 going back to the near-starting levels only after the end of the operational durations at points III and IV respectively.

The compound frequencies include at least one frequency equal to or greater than the cut-off frequency which improves the disinfection performance of the PUV device 100 by maximizing the UV output of the UV lamp 120. For example, the pulsed-output signal 212 at a set frequency (F) of 28 Hz for 3 minutes (T) with an energy of 30 Joules per pulse (Ep) may drive the UV lamp 120 to produce a total UV energy (E=F×Ep×T) of 151.2 KJ. However, for the same total period of 3 minutes and same energy per pulse, the pulsed-output signal 212 at the compound frequencies of 28 Hz (F1) and 29 Hz (F2), each for 0.5 seconds, may drive the UV lamp 120 to produce a total UV energy [E=(F1×Ep×T1)+(F2×Ep×T2)] of 75.6 KJ+78.3 KJ=153.9 KJ, which is greater than the UV output with the pulsed-output signal 212 at a set frequency or single frequency. Moreover, the compound frequencies assist to improve the electrical performance of the PUV device 100, since the input current is being held below the cut-off current for the operational period to prevent the circuit breaker 204 from tripping, despite driving a portion of the pulsed-output signal 212 at a frequency equal to or greater than the cut-off frequency.

Further, in some embodiments, the compound frequencies include non-consecutive frequencies. For example, an absolute difference between any two frequencies in the compound frequencies may be greater than one, discussed below in further detail. The pulse generator 208 may configure the pulsed-output signal 212 with the compound frequencies based on one or more control signals received from the performance controller 210.

Figure 10A:
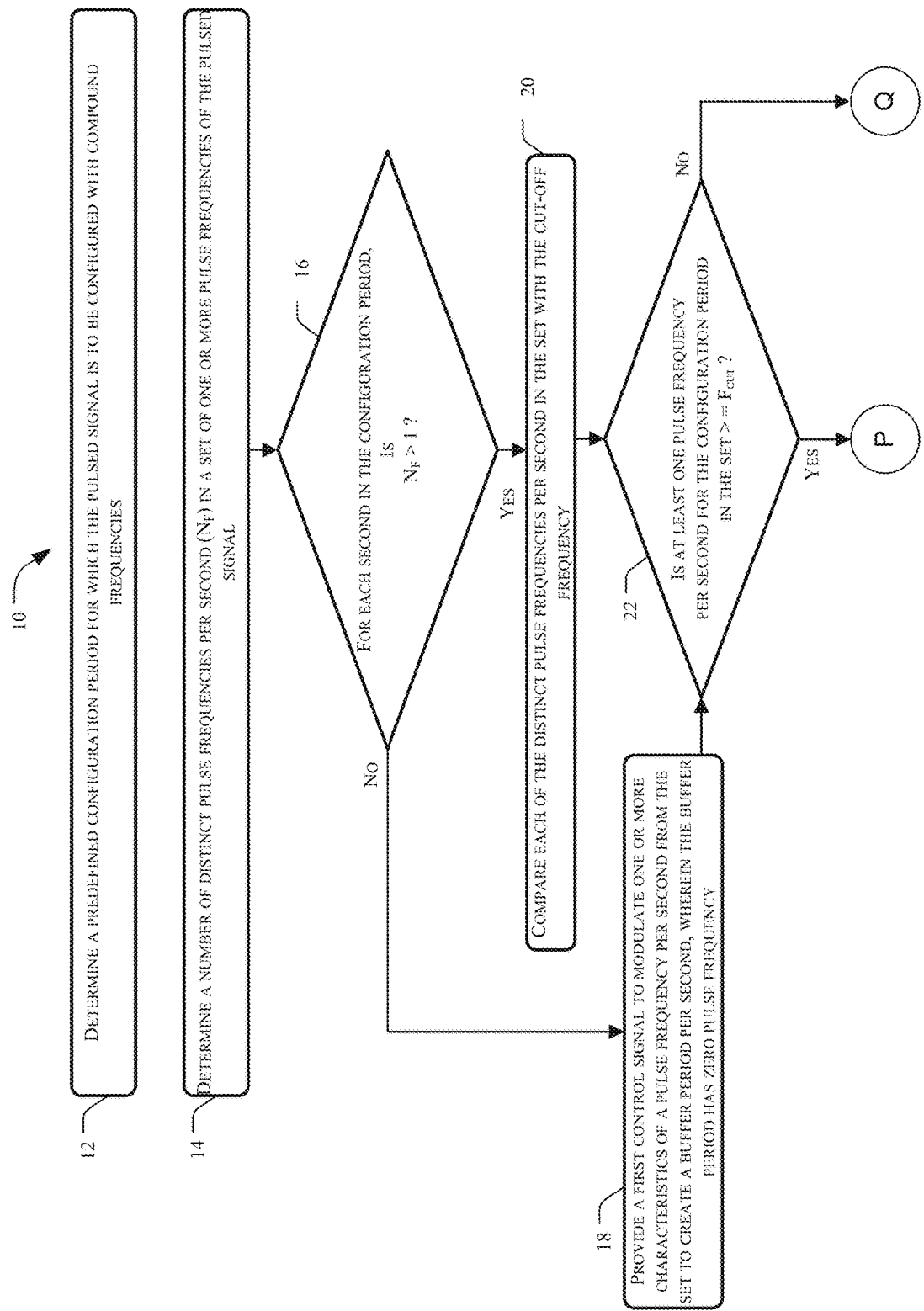
FIGS. 10A-10B are flowcharts illustrating an exemplary method implemented by the performance improvement unit of FIG. 1 for providing one or more control signals to configure a pulse signal with compound frequencies driving the PUV device of FIG. 1 according to an embodiment of the present disclosure.
Figure 10B:
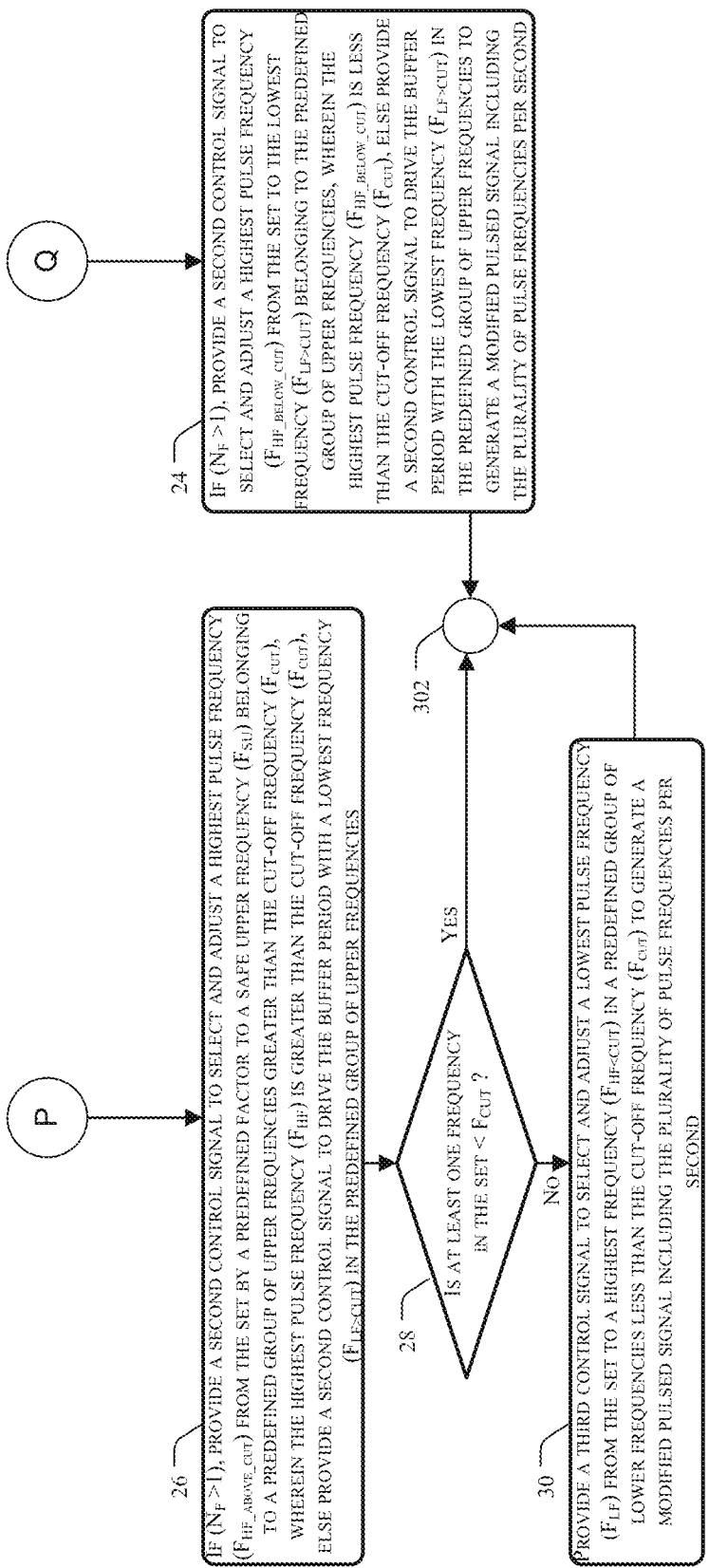

FIGS. 10A-10B are flowcharts illustrating an exemplary method implemented by the performance controller 210 for providing one or more control signals to configure the pulsed-output signal 212 with compound frequencies. The order in which the method 10 is described is not intended to be construed as a limitation, and any number of the described method blocks may be combined, deleted, or otherwise performed in any order to implement the method 10 or an alternate method without departing from the scope and spirit of the present disclosure. The exemplary method 10 may be described in the general context of computer-executable instructions, which may be stored on a computer readable medium, and installed or embedded in an appropriate device for execution. Further, the method 10 may be implemented in any suitable hardware, software, firmware, or combination thereof, that exists in the related art or that is later developed. In one embodiment, the method 10 may be implemented by the performance controller 210. However, one having ordinary skill in the art would understand that aspects of the method 10 may be performed on the pulse generator 208.

At step 12, a predefined period for which the pulsed-output signal 212 is to be configured may be determined. In one embodiment, the performance controller 210 may determine a configuration period for which the pulsed-output signal 212 may be configured with the compound frequencies. The configuration period may be predefined by the performance controller 210 based on a predetermined disinfection cycle or duration; however, in some embodiments, the configuration period may be dynamically defined by a user via a user interface of the PUV device 100. In some other embodiments, the configuration period may be less than the operational period, or the disinfection period or cycle.

At step 14, a number of distinct pulse frequencies per second associated with the pulsed-output signal 212 may be determined. The performance controller 210, in communication with the pulse generator 208, may determine the number of distinct pulse frequencies per second with the pulsed-output signal 212. In one example, the pulsed-output signal 212 may have a single set frequency of 20 Hz. In another example, the pulsed-output signal 212 may be operating with compound frequencies based on being configured in a previous period/cycle, or being manually set therewith by a user via user interface of the PUV device 100.

At step 406, for each second of the configuration period, the performance controller 210 may determine whether or not the number of distinct pulse frequencies per second in the pulsed-output signal 212 being greater than one. Such a determination may assist to assess if the pulsed-output signal 212 requires to be preconditioned for being driven with the compound frequencies. If the number of distinct pulse frequencies per second may be one, i.e., not greater than one, then the performance controller 210 may execute the step 18 for preconditioning the pulsed-output signal 212. However, the performance controller 210 may execute the step 20 if the number of distinct pulse frequencies per second may be greater than one.

At step 18, a first control signal is provided to modulate one or more characteristics of a pulse frequency of the pulsed-output signal 212. In one embodiment, the performance controller 210 may provide a first control signal to the pulse generator 208 for modulating one or more characteristics (e.g., frequency, pulse width, pulse duration, duty cycle, time period, etc.) of the pulsed-output signal 212 having the number of distinct pulse frequencies per second being equal to one. For example, if the pulsed-output signal 212 may have a single frequency per second such as 20 Hz for the configuration period, the performance controller 210 may provide the first control signal to the pulse generator 208. Upon receiving the first control signal, the pulse controller may modulate the pulsed-output signal 212 to create a buffer period per second for the configuration period, where the buffer period of the pulsed-output signal 212 may have zero pulse frequency. For example, the pulse generator 208 may employ a variety of frequency modulation techniques known in the art, related art, or developed later to reduce the time period of the frequency per second by a predefined amount, e.g., 100 ms, 150 ms, 200 ms, 350 ms, 500 ms, etc. to create the buffer period. For instance, if the frequency of the pulsed-output signal 212 is 20 pulses per second or 20 Hz, the pulse generator 208 may reduce the active time period to have the same 20 pulses in 500 ms instead of 1 second. A skilled artisan would understand that any other suitable characteristics of the pulsed-output signal 212 (e.g., pulse width) may also be adjusted for such configuration. The remaining 500 ms of each second within the configuration period may be used as the buffer period having no pulses or zero pulse frequency. In another example, the pulse generator 208 may reduce the active time period while reducing the frequency as well by the same amount. For instance, if the active time period per second is halved to 0.5 seconds, the frequency of 20 pulses may also be halved to 10 pulses for those active 0.5 seconds. The remaining 0.5 seconds for each second within the configuration period may be used as the buffer period. The performance controller 210 may then proceed to execute the step 22.

At step 20, if the number of distinct pulse frequencies per second may be greater than one, the performance controller 210 may compare each of the distinct pulse frequencies per second with the predetermined cut-off frequency. The performance controller 210 may then proceed to execute the step 22.

At step 22, the performance controller 210 may determine if at least one pulse frequency per second with the pulsed-output signal 212 being greater than or equal to the cut-off frequency. In case of the number of distinct pulse frequencies per second with the pulsed-output signal 212 being equal to one as determined in the step 16, the performance controller 210 may check if that single pulse frequency of the pulsed-output signal 212 may be greater than or equal to the cut-off frequency associated with the pulsed-output signal 212. If the number of distinct pulse frequencies per second associated with the pulsed-output signal 212 include at least one frequency greater than or equal to the cut-off frequency, the performance controller 210 may execute the step 26, else the step 24 may be executed.

At step 24, if none of the distinct pulse frequencies per second associated with the pulsed-output signal 212 are greater than or equal to the cut-off frequency, the performance controller 210 may provide a second control signal depending on whether or not the number of distinct pulse frequencies per second determined in step 16 may be greater than one. In one embodiment, if the number of distinct pulse frequencies per second associated with the pulsed-output signal 212 may be greater than one, then the performance controller 210 may provide the second control signal to the pulse generator 208 to perform two steps. In a first step, the pulse generator 208 may be signalled to select a highest pulse frequency from a set of multiple frequencies per second associated with the pulsed-output signal 212. In a second step, the selected highest frequency may be adjusted to be a lowest frequency in a predefined group of upper frequencies, which may include a range of frequencies greater than the cut-off frequency. In one example, if the pulsed-output signal 212 may have frequencies 15 Hz and 20 Hz per second, a cut-off frequency of 29 Hz, and the predefined group of upper frequencies ranging from 30 Hz to 50 Hz, the second control signal may instruct the pulse generator 208 to adjust the highest frequency, i.e., 20 Hz, to the lowest frequency, i.e., 30 Hz, in the predefined group of upper frequencies. A skilled artisan would be able to contemplate any suitable frequency range for the predefined group of upper frequencies and/or a number of frequencies therein. The predefined group of upper frequencies may be determined relative to the cut-off frequency. For example, for a cut-off frequency of 29 Hz, the predefined group of upper frequencies may range from 30 Hz to 50 Hz, 35 Hz to 50 Hz, 40 Hz to 50 Hz, 45 Hz to 50 Hz, and so on.

In another embodiment, if the number of distinct pulse frequencies per second associated with the pulsed-output signal 212 may be equal to one, the second control signal may instruct the pulse generator 208 to the drive the buffer period, which was created in the pulsed-output signal 212 based on the first control signal at step 18, with the lowest frequency in the predefined group of upper frequencies. Once the pulsed-output signal 212 may be adjusted for being driven with compound frequencies, the performance controller 210 in communication with the pulse controller may execute the step 302 to continue monitoring the input current across the circuit breaker 204.

At step 26, if at least one of the distinct pulse frequencies per second associated with the pulsed-output signal 212 are greater than or equal to the cut-off frequency, the performance controller 210 may provide a second control signal depending on whether or not the number of distinct pulse frequencies per second determined in step 16 may be greater than one. In one embodiment, if the number of distinct pulse frequencies per second associated with the pulsed-output signal 212 may be greater than one, then the performance controller 210 may provide the second control signal to the pulse generator 208 to perform two steps. In a first step, the pulse generator 208 may be signalled by the second control signal to select a highest pulse frequency from a set of multiple frequencies per second associated with the pulsed-output signal 212. In a second step, the selected highest frequency may be adjusted or varied reduced by a predefined or dynamically defined factor, to a safe upper frequency belonging to the predefined group of upper frequencies, which may include a range of frequencies greater than the cut-off frequency. In one example, the pulsed-output signal 212 may have frequencies 35 Hz and 45 Hz per second, a cut-off frequency of 29 Hz, and the predefined group of upper frequencies ranging from 30 Hz to 50 Hz. The second control signal may instruct the pulse generator 208 to reduce the highest frequency, i.e., 45 Hz, by a predefined or dynamically defined factor such as 1, 2, 3, 4, 5, 6, . . . , 10, and so on, such that the reduced frequency belongs to the predefined group of upper frequencies. For instance, the highest frequency, i.e., 45 Hz, may be reduced by 2 to an adjusted highest frequency of 43 Hz. In some embodiments, the pulse generator 208 may further reduce the safe upper frequency by 2 if an absolute difference of the safe upper frequency and any other distinct pulse frequency in the compound frequencies may be equal to one. In some embodiments, the safe upper frequency may always be greater than the cut-off frequency. For instance, the safe upper frequency may always be equal to or greater than the lowest frequency in the predefined group of upper frequencies. In another instance, the safe upper frequency may be less than the lowest frequency in the predefined group of upper frequencies but greater than the cut-off frequency.

In another embodiment, if the number of distinct pulse frequencies per second associated with the pulsed-output signal 212 may be equal to one, the second control signal may instruct the pulse generator 208 to the drive the buffer period, which was created in the pulsed-output signal 212 based on the first control signal in step 18, with the lowest frequency (e.g., 30 Hz) belonging to the predefined group of upper frequencies. Once the pulsed-output signal 212 has been adjusted to have at least two distinct pulse frequencies per second for the configuration period with at least one frequency above the cut-off frequency, the performance controller 210 may execute the step 28.

At step 28, the performance controller 210 may determine whether or not the distinct number of frequencies per second (or compound frequencies) associated with the pulsed-output signal 212 include at least one frequency less than the cut-off frequency. If the compound frequencies include at least one frequency less than the cut-off frequency, the performance controller 210 in communication with the pulse controller may execute the step 302 to continue monitoring the input current across the circuit breaker 204. Else, the performance controller 210 may execute the step 30.

At step 30, if the adjusted pulsed-output signal 212 being driven with the compound frequencies includes no frequency per second within the configuration period being less than the cut-off frequency, then the performance controller 210 may provide a third control signal to the pulse generator 208. The third control signal may instruct the pulse generator 208 to select and adjust a lowest frequency in the compound frequencies to a highest frequency in a predefined group of lower frequencies, which may include a range of frequencies less than the cut-off frequency. In the above example of the pulsed-output signal 212 having compound frequencies including 35 Hz and the adjusted frequency of 43 Hz per second, the cut-off frequency being 29 Hz, and a predefined group of lower frequencies ranging from 1 Hz to 28 Hz, the third control signal may instruct the pulse generator 208 to reduce the lowest frequency, i.e., 35 Hz, to a highest frequency, i.e., 28 Hz, belonging to the predefined group of lower frequencies. A skilled artisan would be able to contemplate any suitable frequency range for the predefined group of lower frequencies and/or a number of frequencies therein. The predefined group of lower frequencies may be determined relative to the cut-off frequency. For example, if the cut-off frequency is 29 Hz, the predefined group of lower frequencies may range from 10 Hz to 28 Hz, 15 Hz to 28 Hz, 20 Hz to 28 Hz, 10 Hz to 20 Hz, 2 Hz to 10 Hz, and so on. Once the pulsed-output signal 212 is adjusted for being driven with compound frequencies including at least one frequency equal to or greater than the cut-off frequency and at least one frequency less than the cut-off frequency, the performance controller 210 in communication with the pulse controller may execute the step 302 to continue monitoring the input current across the circuit breaker 204.

While the foregoing written description of the present disclosure enables one of ordinary skill to make and use what is considered presently to be the best mode thereof, those of ordinary skill will understand and appreciate the existence of variations, combinations, and equivalents of the specific embodiment, method, and examples herein. The present disclosure should therefore not be limited by the above described embodiments, methods, and examples, but by all embodiments and methods within the scope and spirit of the present disclosure. Notably, the figures and examples are not meant to limit the scope of the present disclosure to a single embodiment, but other embodiments are possible by way of interchanging some or all of the described or illustrated elements based on the concepts described herein.

The invention claimed is:

1. A method of operating a pulsed ultraviolet (UV) device, the method comprising:
provcurrent uponiding an input current from a power source to a UV source via a component operating to inhibit the input exceeding a predefined cut-off current;
generating, using a pulse generator, a pulse signal for driving the UV source, the pulse signal being associated with a predetermined cut-off frequency, wherein the generated pulse signal upon having a single pulse frequency causes the input current to increase beyond the predefined cut-off current based on the single pulse frequency exceeding the cut-off frequency; and
configuring, using the pulse generator, the generated pulse signal to include a set of distinct pulse frequencies for a predefined period based on the input current exceeding a predefined threshold current, the set of distinct pulse frequencies assisting in increasing the intensity of UV light generated by the UV source, wherein the threshold current is less than the predefined cut-off current.

2. The method of claim 1, wherein the set of distinct pulse frequencies includes a first pulse frequency greater than or equal to the cut-off frequency and a second pulse frequency less than the cut-off frequency.

3. The method of claim 1, wherein the set of distinct pulse frequencies include non-consecutive pulse frequencies, wherein an absolute difference between any two pulse frequencies in the set is greater than one.

4. The method of claim 1, wherein the input current to the UV source upon exceeding the predefined cut-off current is interrupted by the component including one of a circuit breaker and a switching device.

5. The method of claim 1, wherein the step of generating further comprises:
receiving, using a power management unit, a power signal delivering the input current;
manipulating, using the power management unit, an electrical parameter of the power signal, wherein the electrical parameter includes at least one of voltage and current; and
providing, using the power management unit, the manipulated power signal to charge a capacitor of the pulse generator operating to discharge the charged capacitor for generating the pulse signal.

6. The method of claim 5, wherein the manipulated power signal is provided at a constant voltage to the pulse generator.

7. The method of claim 1, wherein the predefined period is shorter than a total operational period of the UV source or a device including the UV source.

8. The method of claim 1, further comprising conditioning, using the pulse generator, the generated pulse signal to include one or more pulses with a square, rectangular, triangular, or spike shape.

9. The method of claim 1, wherein the step of configuring further comprises varying, using a controller in communication with the pulse generator, a combination of distinct pulse frequencies in the set to prevent the input current from exceeding the predefined cut-off current.

10. The method of claim 1, wherein the step of configuring further comprises:
receiving, using the pulse generator, a set of one or more control signals including at least one of a first control signal and a second control signal from a controller, and
manipulating, using the pulse generator, the generated pulse signal based on the received set of one or more control signals in one of the predefined modes including a first mode and a second mode, wherein the step of manipulating includes:
in the first mode:
modulating, using the pulse generator, one or more characteristics of the generated pulse signal having the single pulse frequency based on the first control signal to create a buffer period within the predefined period, the buffer period having zero frequency, wherein the one or more characteristics include at least one of a frequency, pulse width, duty cycle, and time period, and
driving, using the pulse generator, the buffer period with a lowest frequency in a predefined group of upper frequencies based on the second control signal if the single pulse frequency is less than the predefined cut-off frequency, wherein the predefined group of upper frequencies are greater than the predefined cut-off frequency, and
in the second mode:
selecting, using the pulse generator, a highest frequency in the set of distinct pulse frequencies of the generated pulse signal based on the first control signal, wherein the highest frequency is greater than the predefined cut-off frequency,
adjusting, using the pulse generator, the selected highest frequency by a predefined factor to a safe upper frequency belonging to the predefined group of upper frequencies,
selecting, using the pulse generator, a lowest frequency in the set of distinct pulse frequencies of the generated pulse signal based on the second control signal, wherein the lowest frequency is less than the predefined cut-off frequency, and
adjusting, using the pulse generator, the selected lowest frequency to a highest frequency in a predefined group of lower frequencies that are less than the predefined cut-off frequency.

11. A pulsed ultraviolet (UV) device, comprising:
a UV source for generating pulsed UV light;
a component in electrical communication with a power source providing an input current to the UV source, wherein the component is configured to inhibit the input current upon exceeding a predefined cut-off current; and
a pulse generator in electrical communication with the component and the UV source, wherein the pulse generator is configured to
generate a pulse signal for driving the UV source, the pulse signal being associated with a predetermined cut-off frequency, wherein the generated pulse signal upon having a single pulse frequency causes the input current to increase beyond the predefined cut-off current based on the single pulse frequency exceeding the cut-off frequency, and
configure the generated pulse signal to include a set of distinct pulse frequencies for a predefined period based on the input current exceeding a predefined threshold current, the set of distinct pulse frequencies increasing the intensity of pulsed UV light, wherein the threshold current is less than the predefined cut-off current.

12. The device of claim 11, wherein the set of distinct pulse frequencies includes a first pulse frequency greater than or equal to the cut-off frequency and a second pulse frequency less than the cut-off frequency.

13. The device of claim 11, wherein the set of distinct pulse frequencies include non-consecutive pulse frequencies, wherein an absolute difference between any two pulse frequencies in the set is greater than one.

14. The device of claim 11, wherein the component is further configured to interrupt the input current to the UV source upon exceeding the predefined cut-off current, wherein the component includes one of a circuit breaker and a switching device.

15. The device of claim 11, further comprises:
a power management unit in communication with the pulse generator, wherein the power management unit is configured to:
receive a power signal delivering the input current;
manipulate an electrical parameter of the received power signal, wherein the electrical parameter includes at least one of voltage and current; and
provide the manipulated power signal to charge a capacitor of the pulse generator configured to discharge the charged capacitor for generating the pulse signal.

16. The device of claim 15, wherein the manipulated power signal is provided at a constant voltage to the pulse generator.

17. The device of claim 11, wherein the predefined period is shorter than a total operational period of the UV source or the pulsed UV device.

18. The device of claim 11, the pulse generator is further configured to condition the generated pulse signal to include one or more pulses with a square, rectangular, triangular, or spike shape.

19. The device of claim 11, further comprises a controller in communication with the pulse generator, wherein the controller is configured to vary a combination of distinct pulse frequencies in the set to prevent the input current from exceeding the predefined cut-off current.

20. The device of claim 11, wherein the pulse generator is further configured to:
- receive a set of one or more control signals including at least one a first control signal and a second control signal from a controller, and
- manipulate the generated pulse signal based on the received set of one or more control signals in one of the predefined modes including a first mode and a second mode, wherein the pulse generator operates to:
  in the first mode:
  - modulate one or more characteristics of the generated pulse signal having the single pulse frequency based on the first control signal to create a buffer period within the predefined period, the buffer period having zero frequency, wherein the one or more characteristics include at least one of a frequency, pulse width, duty cycle, and time period, and
  - drive the buffer period with a lowest frequency in a predefined group of upper frequencies based on the second control signal if the single pulse frequency is less than the predefined cut-off frequency, wherein the predefined group of upper frequencies are greater than the predefined cut-off frequency, and
  in the second mode:
  - select a highest frequency in the set of distinct pulse frequencies of the generated pulse signal based on the first control signal, wherein the highest frequency is greater than the predefined cut-off frequency,
  - adjust the selected highest frequency by a predefined factor to a safe upper frequency belonging to the predefined group of upper frequencies,
  - select a lowest frequency in the set of distinct pulse frequencies of the generated pulse signal based on the second control signal, wherein the lowest frequency is less than the predefined cut-off frequency, and
  - adjust the selected lowest frequency to a highest frequency in a predefined group of lower frequencies that are less than the predefined cut-off frequency.

* * * * *